(12) United States Patent
Qian et al.

(10) Patent No.: US 12,404,413 B2
(45) Date of Patent: Sep. 2, 2025

(54) BIO-INK STRUCTURES AND METHODS OF PRODUCING THE SAME

(71) Applicant: Lawrence Livermore National Security, LLC, Livermore, CA (US)

(72) Inventors: Fang Qian, Santa Cruz, CA (US); Sarah Baker, Dublin, CA (US); Joshua R. Deotte, Livermore, CA (US); Eric Duoss, Dublin, CA (US); Jennifer Marie Knipe, Oakland, CA (US); Samantha Ruelas, Newberry Springs, CA (US); Christopher Spadaccini, Oakland, CA (US); Joshuah K. Stolaroff, Oakland, CA (US); Cheng Zhu, Livermore, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 1743 days.

(21) Appl. No.: 16/153,501

(22) Filed: Oct. 5, 2018

(65) Prior Publication Data

US 2020/0109299 A1    Apr. 9, 2020

(51) Int. Cl.
| | |
|---|---|
| C09D 11/03 | (2014.01) |
| B29C 64/106 | (2017.01) |
| B29K 105/16 | (2006.01) |
| B33Y 10/00 | (2015.01) |
| B33Y 70/00 | (2020.01) |
| C09D 11/101 | (2014.01) |
| C12P 7/06 | (2006.01) |

(52) U.S. Cl.
CPC ............ *C09D 11/03* (2013.01); *B29C 64/106* (2017.08); *B33Y 10/00* (2014.12); *B33Y 70/00* (2014.12); *C09D 11/101* (2013.01); *C12P 7/06* (2013.01); *B29K 2105/16* (2013.01)

(58) Field of Classification Search
CPC ....... C09D 11/03; C09D 11/101; B33Y 10/00; B33Y 70/00; B29C 64/106; C12P 7/06; B29K 2105/16
See application file for complete search history.

(56) References Cited

PUBLICATIONS

Gopinathan, "Recent trends in bioinks for 3D printing". Biomaterials Research vol. 22, Article No. 11 (Apr. 6, 2018) <URL: https://biomaterialsres.biomedcentral.com/articles/10.1186/s40824-018-0122-1> (Year: 2018).*
Perez-Luna, "Encapsulation of Biological Agents in Hydrogels for Therapeutic Applications". Gels, 4(3), 61 (Jul. 11, 2018) <URL: https://www.mdpi.com/2310-2861/4/3/61/htm> (Year: 2018).*
Schaffner, "3D printing of bacteria into functional complex materials". Science Advances, 3(12) (Dec. 1, 2017) <URL: https://www.science.org/doi/10.1126/sciadv.aao6804> (Year: 2017).*

(Continued)

*Primary Examiner* — Louise W Humphrey
*Assistant Examiner* — Candice Lee Swift
(74) *Attorney, Agent, or Firm* — Perkins Coie LLP

(57) ABSTRACT

Bio-ink comprising freeze-dried cells, methods of making a living structure from a bio-ink material of freeze-dried cells, and methods of using the living structure for biosensing, tissue regeneration, environment sensing, drug discovery, catalysis, and/or clinical implementation are described herein.

20 Claims, 19 Drawing Sheets

(56) References Cited

PUBLICATIONS

OPS Diagnostics, "Bacteria Lyophilization Overview". Retrieved from The Wayback Machine (Aug. 11, 2017) <URL: https://web.archive.org/web/20170811020121/https://opsdiagnostics.com/notes/ranpri/bacteria_lyophilization_overview.htm> (Year: 2017).*
Han, Ying, et al. "Improved preservation of human red blood cells by lyophilization." Cryobiology 51.2 (2005): 152-164. (Year: 2005).*
Guillotin, Bertrand, et al. "Laser assisted bioprinting of engineered tissue with high cell density and microscale organization." Biomaterials 31.28 (2010): 7250-7256. (Year: 2010).*
BioNumbers; https://bionumbers.hms.harvard.edu/bionumber.aspx?id=105906&ver=2&trm=volume+of+a+mammalian+cell&org=; accessed Mar. 21, 2023 (Year: 2023).*
Markstedt, Kajsa, et al. "3D bioprinting human chondrocytes with nanocellulose-alginate bioink for cartilage tissue engineering applications." Biomacromolecules 16.5 (2015): 1489-1496. (Year: 2015).*
Argüelles, Juan Carlos. "Physiological roles of trehalose in bacteria and yeasts: a comparative analysis." Archives of microbiology 174 (2000): 217-224. (Year: 2000).*
Stewart, Philip S. "Diffusion in biofilms." Journal of bacteriology 185.5 (2003): 1485-1491. (Year: 2003).*
Carvalho, Ana S., et al. "Relevant factors for the preparation of freeze-dried lactic acid bacteria." International Dairy Journal 14.10 (2004): 835-847. (Year: 2004).*
Fonseca, Fernanda, et al. "Collapse Temperature of Freeze-Dried Lactobacillus bulgaricusSuspensions and Protective Media." Biotechnology progress 20.1 (2004): 229-238. (Year: 2004).*
Ruka, Dianne R., George P. Simon, and Katherine M. Dean. "Altering the growth conditions of Gluconacetobacter xylinus to maximize the yield of bacterial cellulose." Carbohydrate polymers 89.2 (2012): 613-622. (Year: 2012).*
Santana, Bianca Palma, et al. "Comparing different methods to fix and to dehydrate cells on alginate hydrogel scaffolds using scanning electron microscopy." Microscopy research and technique 78.7 (2015): 553-561. (Year: 2015).*
Runyon, Daniel E., and Adam Z. Higgins. "The Effect of Human Serum Albumin and Hematocrit on the Cake Collapse Temperature of Lyophilized Red Blood Cells." Biopreservation and Biobanking 13.5 (2015): 376-378. (Year: 2015).*
Ammar, Mohamed M., et al. "Growth factor release and enhanced encapsulated periodontal stem cells viability by freeze-dried platelet concentrate loaded thermo-sensitive hydrogel for periodontal regeneration." The Saudi Dental Journal 30.4 (2018): 355-364. (Year: 2018).*
Catoira, Marta Calvo, et al. "Overview of natural hydrogels for regenerative medicine applications." Journal of Materials Science: Materials in Medicine 30 (2019): 1-10. (Year: 2019).*
Cleveland museum of art; https://www.clevelandart.org/art/1942.215.3; accessed Oct. 4, 2023 (Year: 2023).*
Barja F. Bacterial nanocellulose production and biomedical applications. J Biomed Res. May 14, 2021;35(4):310-317. doi: 10.7555/JBR.35.20210036. PMID: 34253695; PMCID: PMC8383174. (Year: 2021).*
Choi, Soon Mo, and Eun Joo Shin. "The nanofication and functionalization of bacterial cellulose and its applications." Nanomaterials 10.3 (2020): 406. (Year: 2020).*
Garrido-Fernández, Juan, et al. "Carotenoid production in Lactobacillus plantarum." International journal of food microbiology 140.1 (2010): 34-39. (Year: 2010).*
Nahr, Fatemeh Keivani, et al. "Optimization of the nanocellulose based cryoprotective medium to enhance the viability of freeze dried Lactobacillus plantarum using response surface methodology." LWT-food Science and Technology 64.1 (2015): 326-332. (Year: 2015).*
Li, Chao, et al. "Yogurt starter obtained from Lactobacillus plantarum by spray drying." Drying Technology 30.15 (2012): 1698-1706. (Year: 2012).*
Barry, R. et al., J. A. Adv. Mater. 2009, 21, 1-4.
Cavallo, A. et al., "Photo-crosslinked poly(ethylene glycol) diacrylate (PEGDA) hydrogels from low molecular weight prepolymer: Swelling and permeation studies," J. Appl. Polym. Sci. 2017, 134, 44380.
Espinosap-Hoyos, D. et al., "Engineered 3D-printed artificial axons," Sci. Rep. Jan. 1, 20181, 8(1): 478.
Ghosh, S. et al., "Direct-Write Assembly of Microperiodic Silk Fibroin Scaffolds for Tissue Engineering Applications." 2008 Advanced Functional Materials 18: 1883-1889.
Gu, Q. et al., "3D Bioprinting Human Induced Pluripotent Stem Cell Constructs for In Situ Cell Proliferation and Successive Multilineage Differentiation," Advanced Healthcare Materials, Sep. 2017, 6(17).
Hanson-Shepherd, J. et al., "3D Microperiodic Hydrogel Scaffolds for Robust Neuronal Cultures," Adv Funct Mater. Jan. 7, 2011;21(1):47-54.
Knowlton, S. et al., "Bioprinting for cancer research," Trends Biotechnol. Sep. 2015;33(9):504-13.
Kolesky, D. et al., "3D bioprinting of vascularized, heterogeneous cell-laden tissue constructs," Adv Mater. May 21, 2014;26(19):3124-30.
Kolesky, D. et al., "Three-dimensional bioprinting of thick vascularized tissues," J. A. Proc. Natl. Acad. Sci. USA Mar. 22, 2016, 113(12), pp. 3179-3184.
Laronda, M. et al., " A bioprosthetic ovary created using 3D printed microporous scaffolds restores ovarian function in sterilized mice," Nature Communications, May 16, 2017, 8, 15261.
Lehner, B. et al., "A Straightforward Approach for 3D Bacterial Printing," ACS Synth Biol. Jul. 21, 2017;6(7):1124-1130.
Liu, X. et al., "3D Printing of Living Responsive Materials and Devices," Adv Mater. Jan. 2018;30(4).
Mahazar, N. et al., "Optimization of Culture Medium for the Growth of Candida sp. and Blastobotrys sp. as Starter Culture in Fermentation of Cocoa Beans (Theobroma cacao) Using Response Surface Methodology (RSM)," Pakistan Journal of Biological Sciences 2017, 20, 154-159.
Murphy, S. et al., "3D bioprinting of tissues and organs," Nat. Biotechnol. 2014, 32, 773-785.
N'Guessan, F. et al., Food Science & Nutrition 2016, 4, (1), 34-41.
Passieux, R. et al., "Instability-Assisted Direct Writing of Microstructured Fibers Featuring Sacrificial Bonds," Adv Mater. Jun. 24, 2015;27(24):3676-80.
Sabins, A. et al., "Cytocompatibility Studies of an in situ Photopolymerized Thermoresponsive Hydrogel Nanoparticle System using Human Aortic Smooth Muscle Cells," J Biomed Mater Res A. Oct. 2009; 91(1): 52-59.
Saha, A. et al., "Additive Manufacturing of Catalytically Active Living Materials," ACS Appl. Mater. Interfaces, 2018, 10(16), pp. 13373-13380.
Schaffner, M. et al., "3D printing of bacteria into functional complex materials," Science advances 2017, 3(12), eaao6804.
Siqueira, D et al., "Cellulose Nanocrystal Inks for 3D Printing of Textured Cellular Architectures." Advanced Functional Materials 2017, 1604619, 10 pages.
Zhang, Y. et al., "Bioprinting the Cancer Microenvironment," ACS Biomater Sci Eng. Oct. 10, 2016;2(10):1710-1721.
Gungor-Ozkerim, et al., "Bioinks for 3D bioprinting: an overview," Biomater. Sci. May 1, 2018; 6(5): 915-946. doi:10.1039/c7bm00765e.

* cited by examiner

BIO-INK STRUCTURES AND METHODS OF PRODUCING THE SAME

STATEMENT REGARDING FEDERAL FUNDING

This invention was made with government support under DE-AC52-07NA27344 awarded by the Department of Energy. The government has certain rights in this invention.

BACKGROUND

Bioprinting is a fabrication technology that can lead to the development of complex three-dimensional (3D) scaffolds containing living cells, which are useful for wide range of applications including biosensing, tissue regeneration, environment sensing, drug discovery and clinical implementation.

SUMMARY

In some aspects, the present disclosure provides bio-inks comprised of a filler of freeze-dried cells.

In another aspect, the present disclosure provides living structures made from a bio-ink comprised of a filler of freeze-dried cells.

In yet another aspect, the present disclosure provides methods of using a living structure made from a filler comprised freeze-dried cells for biosensing, tissue regeneration, environment sensing, drug discovery, catalysis, and/or clinical implementation.

In some embodiments, the filler of freeze-dried cells are microbes. In some embodiment, the microbes are selected from the group consisting of bacteria, algal, fungi, protozoa, and a mixture thereof.

In some embodiments, the filler of freeze-dried cells and/or the living structure of freeze-dried cells has a cell density of at least about 5 wt %, about 10 wt %, about 20 wt %, about 30 wt %, about 40 wt %, about 50 wt %, about 60 wt %, about 70 wt %, about 80 wt %, about 85 wt %, about 90 wt %, about 95 wt % or more of the total weight of the bio-ink or at least about 5 vol %, about 10 vol %, about 20 vol %, about 30 vol %, about 40 vol %, about 50 vol %, about 60 vol %, about 70 vol %, about 75 vol %, about 80 vol %, about 85 vol %, about 90 vol %, about 95 vol %, or more of the total volume of the bio-ink.

In some embodiments, the filler is a single filler or a dual filler. In some embodiments, the dual filler comprises freeze-dried live cells and a dual filler component. In some embodiments, the dual filler is cellulose selected from the group consisting of nanocellulose, cellulose nanocrystals (CNC), cellulose nanofibrils (CNF) bacterial cellulose (BC), and nanocellulose crystalline powder.

In some embodiments, the bio-ink further comprises a hydrogel.

In another aspect, the present disclosure provides methods of making a living structure comprises use of the bio-ink. In some embodiments, the method further comprises seeding at least one additional cell into the living structure.

In some embodiments, the living structure is three dimensional (3D), a lattice, a scaffold, and/or porous.

In some embodiments, at least a portion of the freeze-dried cells are encapsulated in the living structure.

In some embodiment, the living structure maintains cell viability and/or is metabolically active for at least about 1 month, about 2 months, about 3 months, 4 months, about 6 months, about 8 months, or about 10 months.

In some embodiments, the living structure has a resolution of at least about 10 µm, 20 µm, about 40 µm, about 50 µm, about 80 µm, about 100 µm, about 200 µm, about 300 µm, about 400 µm, and/or about 500 µm.

In some embodiments, the living structures has a tunable intracellular distance and/or exhibits high mass transport.

In some embodiments, the living structure mimics morphology, intercellular interactions, signaling pathway activation, and/or diffusion of cells by performing cellular functions selected from the group consisting of cell proliferation, gene expression, protein expression, and responding to external stimuli.

In some embodiments, the catalysis is biocatalysis selected from the group consisting of food fermentation, biofuel production, protein synthesis, wastewater treatment, and bioremediation.

These and other embodiments of the present disclosure will be disclosed in further detail herein below.

DETAILED DESCRIPTION

Figure 1:
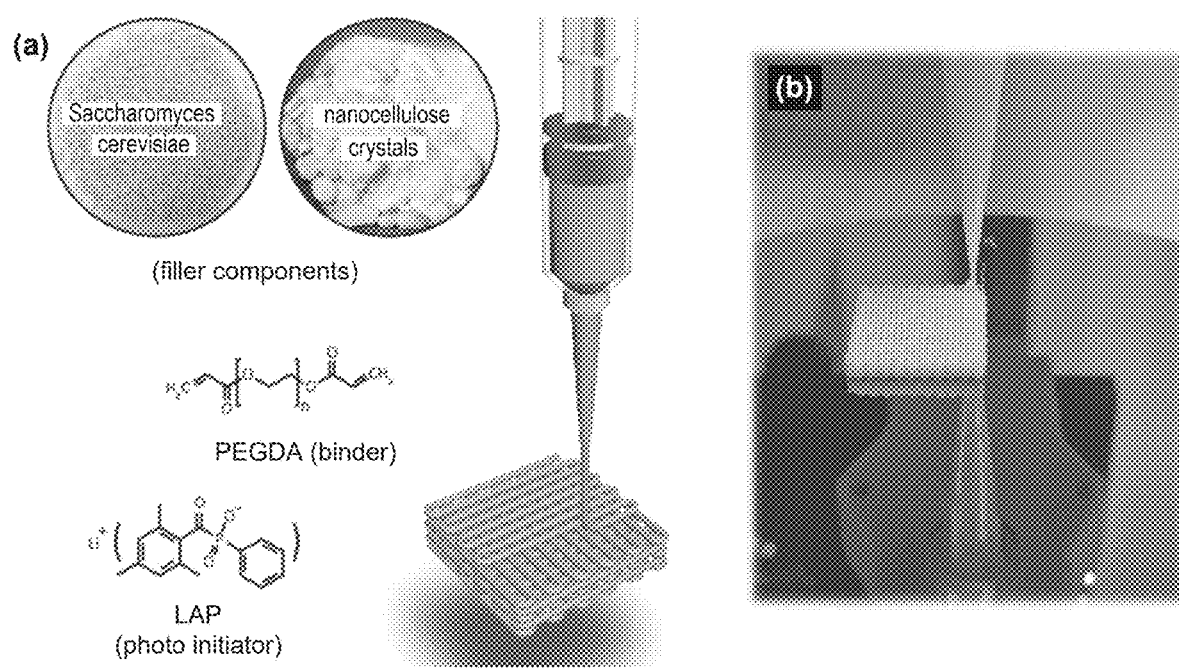
FIG. 1A is a schematic of a bio-ink material according to an embodiment of the present disclosure.
FIG. 1B is a representative photograph of the printing of a structure.

There is a growing interest in the integration of functional microbes into printed structures as it is contemplated that microbes offer advantages in the field of catalysis such as the conversion of various carbon sources into high valuable end-product chemicals. However, current technologies are limited by low cell density, slow mass transport, poor geometric control, and inefficient nutrient acquisition. Conventional techniques (e.g., the addition of a diluted cell suspension to a hydrogel ink solution) result in bio-inks and printed structures with low cell densities. In addition, while ink biocompatibility (i.e., impact of ink materials on cells) has been extensively studied, the impact of cells on ink properties remains unknown, largely because the cell-to-ink impact is negligible when cell density is low. Furthermore, without an ability to directly print cells, the living structure geometries are limited to bulk monolithic geometries such as two dimensional (2D) structures (i.e., flat sheets) with limited control of porosity, mass transport, and nutrient acquisition.

From the foregoing, it will be appreciated that specific embodiments of the invention have been described herein for purposes of illustration, but that various modifications may be made without deviating from the scope of the invention. Accordingly, the invention is not limited except as by the appended claims.

Definitions

As used herein the following terms have the following meanings:

The term "about" when used before a numerical designation, e.g., temperature, time, amount, concentration, and such other, including a range, indicates approximations which may vary by (+) or (−) 10%, 5% or 1%.

Also as used herein, "and/or" refers to and encompasses any and all possible combinations of one or more of the associated listed items, as well as the lack of combinations when interpreted in the alternative ("or").

"Comprising" or "comprises" is intended to mean that the compositions, for example bio-inks and living structures, and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

Compositions

Aspects of the present disclosure are directed to biologically-based inks (referred to herein as "bio-inks") containing cells.

In some embodiments, the bio-inks are comprised of freeze-dried, lyophilized, desiccated, cryodesiccated, and/or dehydrated cells. In another embodiment, the cells are live freeze-dried cells.

The cells of the present disclosure can be any cell type. In some embodiments, the cells are microbes. In some embodiments, the microbes are catalysts. The use of microbes as catalyst offers advantages such mild reaction conditions, self-sustainability, cost-effectiveness, and high catalytic specificity and efficiency relative to conventional inorganic catalysts. Non-limiting examples of microbes include bacteria, algal, fungi, and protozoa cells. The bacteria may be chlorella, dunaliella, Escherichia coli, Lactobacillus acidophilus, Pseudomonas putida, or Bacillus subtilis. In some embodiments, the cells are yeast. Non-limiting examples of yeast cells include Saccharomyces cerevisiae, Candida albicans, torula, Saccharomyces boulardii, Schizosaccharomyces pombe, Cryptococcus neoformans, Saccharomyces pastorianus, Candida glabrata, Pichia pastoris, Candida tropicalis, Zygosaccharomyces rouxii, Candida parapsilosis, Issatchenkia orientalis, Pichia guilliermondii, Brettanomyces bruxellensis, Candida lusitaniae, Cryptococcus gattii, Torulaspora delbrueckii, Zygosaccharomyces bailii, Brettanomyces claussenii, Candida auris, Candida stellata, Candida viswanathii, Geotrichum candidum, Saccharomyces exiguous, Kluyveromyces marxianus, Saccharomyces telluris, Leucosporidium frigidum, Leucosporidium frigidum, Candida dubliniensis, Rhodotorula glutinis, Yarrowia lipolytica, Yarrowia lipolytica, Saccharomyces bayanus, Candida blankii, Kluyveromyces lactis, Trichosporon beigelii, Eremothecium gossypii, Ogataea polymorpha, Rhodotorula rubra, Pichia stipites, Candida antarctica, Candida humilis, Candida oleophila, Lachancea kluyveri, Saccharomyces florentinus, Trichosporon mycotoxinivorans, Trichosporon cutaneum, Sporoidiobolus salmonicolor, Sporobolomyces salmonicolor, Candida vulgaris, Sporidiobolus johnsonii, and Candida mogii.

In some embodiments, the cells are diatom, plant, avian, fish, amphibian, reptilian or mammalian cells. In some embodiments, the cell may be a prokaryotic or a eukaryotic cell. Non-limiting examples of suitable cells include, chondrocytes, connective osteoprogenitor, osteoblasts, osteoclasts, keratinocytes, hair root, hair shaft, hair matrix, exocrine secretory epithelial, hormone secreting, epithelial, neuronal, neural or sensory, photoreceptor, muscle, extracellular matrix, blood, cardiovascular, endothelial, kidney cells, hepatic, pancreatic, immune, stem, germ, nurse, interstitial, stellate, progenitors, and a combination thereof. The cell may be a mesenchymal stem cell.

In some embodiments, the cells are mammalian cells. Non-limiting examples of mammalian cells include cells from a mouse, a rat, a human, a canine, a bovine, a porcine or feline or a mixture thereof.

In some embodiments, the cells can be genetically modified cells. The cells can be genetically modified according to various methods including, for example, transgene expression vectors, CRISPR, or genome editing. For example, in some embodiments, a cell can be genetically modified to express and secrete a desired compound such as a bioactive agent (e.g., anticancer agent, antibiotic, analgesic, anti-inflammatory agent, immunosuppressant, enzyme inhibitor, antihistamine, muscle relaxant, hormone, antispasmodic, or a vaccine), a growth factor (e.g., platelet-growth factor, transforming growth factor-beta, fibroblast growth factor, or vascular endothelial growth factor), a cytokine (e.g., chemokine, interferon, interleukin, lymphokine, and tumor necrosis factor), or another polypeptide, gene product, or metabolic product of interest.

The bio-ink disclosed and described herein can be have a high cell density. It is contemplated that a high cell density can act, at least in part, to enhance catalytic activity by increasing the rate of the chemical reaction by the incorporation of a larger number of catalytic active sites (i.e., cells). In some embodiments, the cells comprise at least about 5 percent weight (wt %), about 10 wt %, about 15 wt %, about 20 wt %, about 25 wt %, about 30 wt %, about 35 wt %, about 40 wt %, about 45 wt %, about 50 wt % about 55 wt %, about 60 wt %, about 65 wt %, about 70 wt %, about 75 wt %, about 80 wt %, about 85 wt %, about 90 wt %, about 95 wt %, or about 100 wt % of the total weight of the bio-ink. In some embodiments, the cells comprise at least about 5 wt % to about 100 wt %, about 10 wt % to about 100 wt %, about 15 wt % to about 90 wt %, about 20 wt % to about 90 wt %, about 35 wt % to about 80 wt %, about 30 wt % to about 70 wt %, about 40 wt % to about 90 wt %, about 45 wt % to about 75 wt %, about 80 wt % to about 100 wt %, about 80 wt % to about 95 wt %, about 30 wt % to about 90 wt %, about 35 wt % to about 95 wt %, about 50 wt % to about 70 wt %, 50 wt % to about 40 wt %, about 30 wt % to about 75 wt %, about 50 wt % to about 75 wt % of the total weight of the bio-ink.

In some embodiments, the cells comprise at least about 5 percent volume (vol %), about 10 vol %, about 15 vol %, about 20 vol %, about 25 vol %, about 30 vol %, about 35 vol %, about 40 vol %, about 45 vol %, about 50 vol % about 55 vol %, about 60 vol %, about 65 vol %, about 70 vol %, about 75 vol %, about 80 vol %, about 85 vol %, about 90 vol %, about 95 vol %, or about 100 vol % of the total weight of the bio-ink. In some embodiments the cells comprise at least about 5 vol % to about 100 vol %, about 10 vol % to about 100 vol %, about 15 vol % to about 90 vol %, about 20 vol % to about 90 vol %, about 35 vol % to about 80 vol %, about 30 vol % to about 70 vol %, about 40 vol % to about 90 vol %, about 45 vol % to about 75 vol %, about 80 vol % to about 100 vol %, about 80 vol % to about 95 vol %, about 30 vol % to about 90 vol %, about 35 vol % to about 95 vol %, about 50 vol % to about 70 vol %, 50 vol % to about 40 vol %, about 30 vol % to about 75 vol %, about 50 vol % to about 75 vol % of the total volume of the bio-ink.

In some embodiments, cell density is expressed as the number of cells per volume (i.e., $cm^3$) of the bio-ink. In some embodiments, the cell density is about $1.0 \times 10^3$ cells/$cm^3$, about $1.0 \times 10^4$ cells/$cm^3$, about $1.0 \times 10^5$ cells/$cm^3$, about $1.0 \times 10^6$ cells/$cm^3$, about $1.0 \times 10^7$ cells/$cm^3$, about $1.0 \times 10^8$ cells/$cm^3$, about $1.0 \times 10^9$ cells/$cm^3$, about $1.0 \times 10^{10}$ cells/$cm^3$, about $1.0 \times 10^{11}$ cells/$cm^3$, about $1.0 \times 10^{12}$ cells/$cm^3$, about $1.0 \times 10^{13}$ cells/$cm^3$, about $1.0 \times 10^{14}$ cells/$cm^3$, about $1.0 \times 10^{15}$ cells/$cm^3$, about $1.0 \times 10^{16}$ cells/$cm^3$, about $1.0 \times 10^{16}$ cells/$cm^3$, about $1.0 \times 10^{17}$ cells/$cm^3$, about $1.0 \times 10^{18}$ cells/$cm^3$, about $1.0 \times 10^{19}$ cells/$cm^3$, or about $1.0 \times 10^{20}$ cells/$cm^3$. In some embodiments the cell density is between about $1.0 \times 10^3$ cells/$cm^3$ to about $1.0 \times 10^{20}$ cells/$cm^3$, about $1.0 \times 10^8$ cells/$cm^3$ to about $1.0 \times 10^9$ cells/$cm^3$, about $1.0 \times 10^6$ cells/$cm^3$ to about $1.0 \times 10^{13}$ cells/$cm^3$, or about $1.0 \times 10^8$ cells/$cm^3$ to about $1.0 \times 10^{17}$ cells/$cm^3$.

In some embodiments, the bio-ink comprises only one component (i.e., a single filler). In other embodiments, the bio-ink comprises more than one component, for example, two components (i.e., a dual filler), three components, four components, five components, six components, seven components, eight components, nine components, or more.

In some embodiments, the bio-ink comprising more than one filler component (e.g., a dual filler) further comprises cellulose, a plastic, a ceramic, and/or a metal. In some embodiments, the plastic is a polymer. Non-limiting examples of a plastic and/or polymer include acrylonitrile butadiene styrene (ABS), polylactic acid (PLA), polyvinyl alcohol, nylon, polyethylene, high-density polyethylene, polyethylene terephthalate (PET), acrylonitrile styrene acrylate (ASA), and polycarbonate (PC), carbon fiber, thermoplastic elastomer, elastomer, thermoplastic polyurethane, polyurethane, polyamide, lignin, polystyrene, polycaprolactone (PCL), methacrylated hyaluronic acid (meHA), and polypropylene. In some embodiments, the metal is a metal filament and/or a metal alloy. Non-limiting examples of a metal used in accordance with the disclosure include steel, brass, bronze, silver, copper, aluminum, gold, platinum, chromium, cobalt, and titanium. In some embodiments, the metal is a particle and/or nanoparticle. In some embodiments, the cellulose is nanocellulose, cellulose nanocrystals (CNC), cellulose nanofibrils (CNF), bacterial cellulose (BC), and/or nanocellulose crystalline powder. In some embodiments, the ceramic is an inorganic, nonmetallic, solid material comprising metal, nonmetal or metalloid atoms. Non-limiting examples of a ceramic include calcium phosphate salts, glass, metal oxides such as titanium oxide ($TiO_2$), copper oxide ($Cu_2O$), and molybdenum oxide ($MoO_3$). In some embodiments, bio-inks comprising more than one filler component further comprise alginate, chitosan, gelatin, gelatin methacryloyl (GelMA), collagen, and/or fibrin. In some embodiments, alginate, chitosan, gelatin, gelatin methacryloyl (GelMA), collagen, and/or fibrin are expressly excluded.

In some embodiments, the more than one component of a bio-ink comprising more than one filler (e.g., a dual filler) provides structural support and strength to the bio-ink. In one embodiment, the more than one filler component provides cell density tunability of the bio-ink, wherein the cell density can be increased or decreased depending on the amount of the filler component added to the bio-ink material.

In some embodiments, the cells and the more than one filler component (e.g. a dual filler) are present in the bio-ink in a ratio of 1:100 to 100:1, 1:80 to 80:1, 1:70 to 70:1, 1:60 to 60:1, 1:50 to 50:1, 1:40 to 40:1, 1:30 to 30:1, 1:20 to 20:1, 1:10 to 10:1, 2:3 to 3:2, 3:4 to 4:3, 1:4 to 4:1, 1:3 to 3:1, 1:2 to 2:1, or about 1:1 wherein the ratio is either a weight, mass, or molar ratio of the cells to the filler component and/or components. In some embodiments, the cell density of the bio-ink is higher when there are more cells present relative to the more than one filler component.

In some embodiments, the filler further comprises a binder. The binder can be an oligomer, monomer, or mixtures thereof. Non-limiting examples of suitable binders include styrene, methacrylate, vinyl alcohol, polyisobutylene, glycercols, polypropylene, and polyethylene glycol dimethacrylate. In some embodiments, the filler further comprises a photo-initiator. A function of a photo-initiator is to initiate photopolymerization upon irradiation with ultraviolet (UV) light. In one embodiment, the photo-initiator absorbs light and initiates the photopolymerization of the binder material (i.e., the oligomer and/or monomer) to enable the printing and/or fabrication of a living structure.

Non-limiting examples of suitable photo-initiators include 1-hydroxycyclohexyl phenyl ketone (Irgacure 184), 2,2-dimethoxy-2-phenylacetophenone (Irgacure 651), and 2-methyl-1-[4-(methylthio)phenyl]-2-(4-morpholinyl)-1-propanone (Irgacure907), hydroxyacetophenone, phosphineoxide, benzophenone, and lithium phenyl-2,4,6-trimethylbenzoylphosphinate (LAP).

In some embodiments, the cells and the binder are present in the bio-ink in a ratio of 1:100 to 100:1, 1:80 to 80:1, 1:70 to 70:1, 1:60 to 60:1, 1:50 to 50:1, 1:40 to 40:1, 1:30 to 30:1, 1:20 to 20:1, 1:10 to 10:1, 2:3 to 3:2, 3:4 to 4:3, 1:4 to 4:1, 1:3 to 3:1, 1:2 to 2:1, or about 1:1 wherein the ratio is either a weight, mass, or molar ratio of the cells to the binder.

In some embodiments, the more than one filler component (e.g., a dual filler) and the binder are present in the bio-ink in a ratio of about 1:100 to 100:1, 1:80 to 80:1, 1:70 to 70:1, 1:60 to 60:1, 1:50 to 50:1, 1:40 to 40:1, 1:30 to 30:1, 1:20 to 20:1, 1:10 to 10:1, 2:3 to 3:2, 3:4 to 4:3, 1:4 to 4:1, 1:3 to 3:1, 1:2 to 2:1, or about 1:1 wherein the ratio is either a weight, mass, or molar ratio of the filler component and/or components to the binder.

In some embodiments, the cells and the photo-initiator are present in the bio-ink in a ratio of about 1:1000 to 1000:1, 1:900 to 900:1, 1:800 to 800:1, 1:700 to 700:1, 1:600 to 600:1, 1:500 to 500:1, 1:600 to 600:1, 1:700 to 700:1, 1:600 to 600:1, 1:500 to 500:1, 1:400 to 400:1, 1:300 to 300:1, 1:200 to 200:1, 1:100 to 100:1, 1:80 to 80:1, 1:70 to 70:1, 1:60 to 60:1, 1:50 to 50:1, 1:40 to 40:1, 1:30 to 30:1, 1:20 to 20:1, 1:10 to 10:1, 2:3 to 3:2, 3:4 to 4:3, 1:4 to 4:1, 1:3 to 3:1, 1:2 to 2:1, or about 1:1 wherein the ratio is either a weight, mass, or molar ratio of the cells to the photo-initiator.

In some embodiments, the more than one filler component (e.g., a dual filler) and the photo-initiator are present in the bio-ink in a ratio of about 1:100 to 100:1, 1:80 to 80:1, 1:70 to 70:1, 1:60 to 60:1, 1:50 to 50:1, 1:40 to 40:1, 1:30 to 30:1, 1:20 to 20:1, 1:10 to 10:1, 2:3 to 3:2, 3:4 to 4:3, 1:4 to 4:1, 1:3 to 3:1, 1:2 to 2:1, or about 1:1 wherein the ratio is either a weight, mass, or molar ratio of the filler component and/or components to the photo-initiator.

In some embodiments, the binder and photo-initiator are present in a ratio of 1:1000 to 1000:1, 1:900 to 900:1, 1:800 to 800:1, 1:700 to 700:1, 1:600 to 600:1, 1:500 to 500:1, 1:600 to 600:1, 1:700 to 700:1, 1:600 to 600:1, 1:500 to 500:1, 1:400 to 400:1, 1:300 to 300:1, 1:200 to 200:1, 1:100 to 100:1, 1:80 to 80:1, 1:70 to 70:1, 1:60 to 60:1, 1:50 to 50:1, 1:40 to 40:1, 1:30 to 30:1, 1:20 to 20:1, 1:10 to 10:1, 2:3 to 3:2, 3:4 to 4:3, 1:4 to 4:1, 1:3 to 3:1, 1:2 to 2:1, or about 1:1, wherein the ratio is either a weight, mass, or molar ratio of the binder to the photo-initiator.

In one embodiment, the bio-ink further comprises a hydrogel. Non-limiting examples of suitable hydrogels include polyethylene glycol dimethacrylate (PEGDA), polyethylene glycol, alginate, gelatin, glycidyl methacrylate, pluronic F127-di-acrylate (F127-DA), pluronic F127-dimethyl acrylate (F127-DMA), or gelatin methacryloyl. In some embodiments, a hydrogel is expressly excluded from the bio-ink. In some embodiments, the bio-ink comprises no or substantially no hydrogel.

In various embodiments, the bio-ink has thixotropic and viscoelastic properties. Thixotropic properties are observed in materials that are thick and/or viscous under static conditions (e.g., atmospheric temperature and pressure) however upon the application of an external stimuli (e.g., increased pressure, temperature, shaking, and/or shearing), the material becomes thinner and less viscous. Thixotropic properties lead to time-dependent viscosity properties and/or shear thinning behavior. Viscoelastic properties are observed in materials that exhibit both viscous and elastic characteristics when undergoing a transformation caused by the application of external stimuli. For example, upon application of an external stimuli, the material is deformed however, upon removal of the external stimuli, the material returns to its original, non-transformed state. In some embodiments, the bio-ink is thixotropic and/or viscoelastic. In some embodiments, regardless of the cell to the more than one filler component (e.g., a dual filler) ratio, the bio-ink material is thixotropic and/or viscoelastic. In one embodiment, the bio-ink is a shear thinning ink.

In one embodiment, the cells (e.g., freeze-dried cells) and the more than one filler component (e.g., a dual filler) can be used independently to make respective monolith bio-inks (e.g., a bio-ink consisting of only freeze-dried cells or only the dual filler component) as well as in combination at arbitrary ratios. When the cells are used to make a monolith bio-ink, they function as a viscosifier above a specific cell loading of at least about 30 wt % of the total bio-ink. Similarly, when more than one filler component is used alone, the filler component can generate a shear-thinning aqueous based bio-ink. This contrasts previously reported bio-inks with a single filler component where ink printability is tuned by a single parameter (e.g., loading of the inorganic filler or concentration of the polymer solution). However, the presently described bio-ink with more than one filler component enables a more comprehensive control of ink rheology and cell density.

The bio-inks disclosed and described herein can have one or more of the following a filler of freeze-dried cells, high cell density, cell density tunability, thixotropic properties, viscoelastic properties, and a shear thinning ink. In some embodiments the bio-ink comprises microbes (e.g., yeast) having a cell density of at least 50 wt % of the total bio-ink. In some embodiments, the bio-ink comprises microbes having a cell density of at least 50 wt % of the total bio-ink and a cellulose. In another embodiment, the bio-ink is comprised of a single filler. In yet another embodiment, the bio-ink is further comprised of a dual filler where the dual filler is cellulose.

In some embodiments, a sample of cells are obtained from a source (e.g., a mammal, bacterium, algae, protozoa, or fungus), isolated, and dried by methods such as freeze-drying, lyophilization, desiccation, cryodesiccation, sublimation, vacuum (e.g., reduced pressure), or the like. In some embodiments, prior to the drying, the sample of cells is concentrated, for example, via multiple rounds of centrifuging followed by the decanting of exogenous liquids (e.g., water). In another embodiment, the sample of cells is first frozen, after which ice is removed via sublimation under vacuum. In some embodiments, the sample of cells is frozen using an electric freezer, liquid nitrogen, and/or liquid helium. In some embodiments, the sample of cells is frozen at about −10° C., about −20° C., about −30° C., about −40° C., about −50° C., about −60° C., about −70° C., about −80° C., about −90° C., about −100° C., about −110° C., about −120° C., about −130° C., about −140° C., about −150° C., about −160° C., about −170° C., about −180° C., about −190° C., about −200° C., about −210° C., about −220° C., about −230° C., about −240° C., about −250° C., about −260° C., about −270° C., about −280° C., about −290° C., or about −300° C. In some embodiments, the freezing occurs at about −10° C. to about −50° C., about −20° C. to about −300° C., −70° C. to about −300° C., −90° C. to about −270° C., −200° C. to about −270° C., −80° C. to about −250° C., or about −100° C. to about −300° C. In another embodiment, the cryoprotectants are added to the sample of cells to protect the living cells against freezing damage (i.e., growth of ice crystals and/or other stress). In some embodiments, the cryoprotectant is removed from the freeze-dried cells prior to use. In various embodiments, the sample of cells is dried by removal of water from the surrounding environment of the cells. In some embodiments, the removal of water alters the cells from their natural state for example, by altering the surrounding hydrogen-bonding networks.

In some embodiments, the sample of cells is lyophilized. In one embodiment, the sample of cells is lyophilized in the presence of a stabilizer such as galactose, glucose, maltose, raffinose, lactose, inositol, ectoine, and proline, sucrose, trehalose, or any mixture thereof. In some embodiments, the cryoprotectants can replace the hydrogen bonding networks from the water upon dehydration (e.g. removal of the water) of the cells. In some embodiments, the cells are dehydrated without freezing the sample of cells. For example, in some embodiments, the sample of cells is placed under vacuum until water has been removed from the sample (i.e., dehydrated cells). In some embodiments, the cells are dehydrated by the application of heat and vacuum. In some embodiments, the cells can be rehydrated.

Living Structure and Methods of Making the Same

Aspects of the present disclosure are directed to living structures comprised of a bio-ink and methods of making the same.

In some embodiments, the living structure is made of a bio-ink of freeze-dried, lyophilized, desiccated, cryodesiccated, and/or dehydrated cells. In another embodiment, the living structure is made of a bio-ink of live freeze-dried cells.

In some embodiments, at least a portion of the cells of the living structure are incorporated (i.e., encapsulated) into the living structure. In some embodiments, all or substantially all of the cells of the living structure are incorporated (i.e., encapsulated) into the living structure. In another embodiment, the living structures can be printed using whole cells.

In one embodiment, the living structure is biocompatible. A biocompatible, living structure is able to perform a desired function (e.g., provide a medicinal therapy) within a physiological environment without eliciting unwanted and/or adverse effects to the environment (e.g., remain substantially biologically unreactive). In another embodiment, the living structure is biocompatible with respect to both surface and structural properties. In some embodiments, living structures does not release any toxic chemicals, does not induce unnecessary immune, inflammatory, thrombogenic, or fibrogenic responses, and also does not damage and/or effect the surrounding structures of the physiological environment.

In some embodiments, the living structure refers to a lattice or a scaffold. In another embodiment, the living structure is one dimensional (1D), two dimensional (2D), or three dimensional (3D). In yet another embodiment, the living structure is porous. In another embodiment, the living structure is a self-supporting structure.

In some embodiments, the living structure is highly porous. Increased porosity can enhance catalytic activity by enabling the diffusion of substrates into the structure and can also provide a suitable environment for cell nutrient acquisition. In some embodiments, the living structure has a pore diameter of at least about 0.10 µm, about 1.0 µm, about 10 µm, about 50 µm, about 100 µm, about 150 µm, about 200 µm, about 250 µm, about 300 µm, about 350 µm, about 400 µm, about 450 µm, about 500 µm, about 550 µm, about 650 µm, about 700 µm, about 750 µm, about 800 µm, about 850 µm, about 900 µm, about 950 µm, about 1000 µm. In some embodiments, living structure has a pore diameter between about 1.0 to about 500 µm, about 0.10 µm to about 10 µm, about 150 µm to about 1000 µm, about 300 µm to about 600 µm, about 200 µm to about 800 µm, about 300 µm to about 500 µm, about 500 µm to about 1000 µm, or about 600 µm to about 800 µm.

In another embodiment, the living structure is metabolically active. Metabolic activity refers to the ability of the cell to carry out a series of enzyme-catalyzed reactions that occur within the cells, these reactions are collectively referred to as metabolic pathways. Accordingly, metabolically activity diminishes as cell are damaged and/or die. In some embodiments, the cells are metabolically active for at least about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 12 months, or more.

In another embodiment, the living structure maintains cell viability. Cell viability is a measure of the number of live cells as compared to the total number of cells, both dead and alive. Determining cell viability provides an assessment of the effectiveness of the living structure to support living cells relative to inducing cell death. Any method of determining cell viability known to one of skill in the art is suitable. Non-limiting examples include 3-(4,5-dimethylthiazol-2-yl)-2,5-diphenyltetrazolium bromide) (MTT) tetrazolium reduction assays, resazurin reduction assays, protease viability marker assays, ATP assays, and real-time assays. In some embodiments, the cells maintain cell viability for at least about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 12 months, or more. In some embodiments the cells are considered to maintain cell viability if within at least about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 12 months, or more at least about 100%, about 90%, about 80%, about 70%, about 60%, about 50%, about 40%, or at about 30% of the cells are alive relative to the total number of cells in the living structure.

In one embodiment, metabolic activity and/or cell viability can be determined by staining the cells of the living structure with for example, a bacterial stain and then taking confocal microscope images of the living structures. The stain can differentiate between the live and dead cells and through comparison between the live and dead cells, the number of live cells relative to dead cells and/or total cells can be determined.

In another embodiment, the living structure has customizable geometries. Non-limiting customizable geometries include a cube, cylinder, hollow cone, circular translating coil, sphere, torus, cuboid, triangular pyramid, square pyramid, or triangular prism geometry. In some embodiments, the living structure is a cube, cube-like, or substantially cube-like. In yet another embodiment, the living structure is a cylinder, cylinder-like, or substantially cylinder-like. In another embodiment, the living structure is a hollow cone, hollow cone-like, or substantially hollow cone-like. In another embodiment, the living structure is a circular translating coil, circular translating coil-like, or substantially circular translating coil-like. In another embodiment, the living structure is a sphere, sphere-like, or substantially sphere-like. In another embodiment, the living structure is a torus, torus-like, or substantially torus-like. In another embodiment, the living structure is a cuboid, cuboid-like, or substantially cuboid-like. In another embodiment, the living structure is a triangular pyramid, triangular pyramid-like, or substantially triangular pyramid-like. In yet another embodiment, the living structure is a square pyramid, square pyramid-like, or substantially square pyramid-like. In yet another embodiment, the living structure is a triangular prism, triangular prism-like, or substantially triangular prism-like.

In another embodiment, the intercellular distance (i.e., cell to cell distance) within the living structure is tunable. The intercellular density of the living structure can be tuned based on the cell density of the bio-ink. For example, the higher the cell density of the bio-ink, the smaller the intercellular distance whereas the lower the cell density of the bio-ink, the longer the intercellular distance. Accordingly, similar to the cell density tunability of the bio-ink, the intercellular distance is tunable by increasing or decreasing the amount of the one or more filler components added to the bio-ink material. In some embodiments, the intercellular distance is about 0.10 µm, about 0.50 µm, about 1.0 µm, about 1.5 µm, about 2.0 µm, about 2.5 µm, about 3.0 µm, about 3.5 µm, about 4.0 µm, about 4.5 µm, about 5.0 µm, about 5.5 µm, about 6.0 µm, about 6.5 µm, about 7.0 µm, about 7.5 µm, about 8.0 µm, about 8.5 µm, about 9.0 µm, about 9.5 µm, about 10 µm, about 15 µm, about 20 µm, about 25 µm, about 30 µm, about 25 µm, about 30 µm, about 35 µm, about 40 µm, about 45 µm, about 50 µm, about 60 µm, about 70 µm, about 80 µm, about 90 µm, or about 100 µm. In some embodiments, living structure has a pore diameters between about 1.0 to about 10 µm, about 0.10 µm to about 10 µm, about 2.0 µm to about 9.0 µm, about 4 µm to about 8 µm, about 5 µm to about 10 µm, about 0.10 µm to about 2.0 µm, about 3.5 µm to about 7.0 µm, about 0.10 µm to about 6.0 µm, about 0.10 µm to about 100 µm, about 50 µm to about 100 µm, to about 40 to about 70 µm, to about 60 µm to about 100 µm, to about 10 to about 100 µm, or about 30 µm to about 70 µm.

In some embodiments, the living structure has a high resolution. In some embodiments, the bio-ink material is printed, extruded, and/or deposited to form a living structure with high resolution. In some embodiments, the printed living structure is made by printing, extruding, and/or depositing individual layers of the bio-ink that successively stack atop one another without damaging the integrity of the structure and/or the resolution of the printed structure. In some embodiments the living structure has a high resolution of at least about least about 10 µm, about 20 µm, about 40 µm, about 50 µm, about 80 µm, about 100 µm, about 200 µm, about 300 µm, about 400 µm, or about 500 µm. In some embodiments the living structure has a high resolution between about 10 µm to about 500 µm, about 20 µm to about 400 µm, about 50 µm to about 80 µm, about 10 µm to about 30 µm, about 20 µm to about 50 µm, about 30 µm to about 200 µm, or about 40 µm to about 400 µm.

In another embodiment, the living structure is catalytic and/or has catalytic activity. In some embodiments the living structure has a high catalytic activity of at least about 1 g/L, about 2 g/L, about 3 g/L, about 4 g/L, about 5 g/L, about 6 g/L, about 7 g/L, about 8 g/L, about 9 g/L, about 10 g/L, about 11 g/L, about 12 g/L, about 13 g/L, about 14 g/L, about 15 g/L, about 16 g/L, about 17 g/L, about 18 g/L, about 19 g/L, about 20 g/L, about 21 g/L, about 22 g/L, about 23 g/L, about 24 g/L, about 25 g/L, about 26 g/L, about 27 g/L, about 28 g/L, about 29 g/L, about 30 g/L, about 31 g/L, about 32 g/L, about 33 g/L, about 34 g/L, about 35 g/L, about 36 g/L, about 37 g/L, about 38 g/L, about 39 g/L, or about 40 g/L per 0.1 g of bio-ink. In some embodiments, the living structure has a catalytic activity between about 1 g/L to about 40 g/L, about 2 g/L to about 20 g/L, about 10 g/L to about 16 g/L, about 5 g/L to about 32 g/L, 13 g/L to about 16 g/dL, about 5 g/L to about 20 g/L, about 16 g/L to about 30 g/L, or about 3 g/L to about 16 g/L volumetric productivity per 0.1 g of bio-ink.

In another embodiment the living structure has increased catalytic production as compared to conventional printed structures with low cell densities (e.g., structures not formed from freeze-dried cells). In some embodiments, the living structure provides about 2×, about 3×, about 4×, about 5×, about 6×, about 7×, about 8×, about 9×, about 10×, about 20×, about 30×, about 40×, about 50×, about 60×, about 70×, about 80×, about 90×, about 100×, about 110×, about 120×, about 130×, about 140×, about 150×, about 160×, about 170×, about 180×, about 190×, or about 200× increase in catalytic production as compared to conventional printed structures. In some embodiments, the living structure provides about 2× to about 100×, about 10× to about 200×, about 2× to about 10×, about 2× to about 6×, about 70× to about 100×, about 50× to about 150× increase in catalytic production as compared to conventional printed structures. In various embodiments, the catalytic reactions include and/or are relevant to food fermentation, biofuel production, protein synthesis, wastewater treatment, and/or bioremediation. In one embodiment, the living structure increases ethanol production in glucose fermentation.

In another embodiment, the living structure has high mass transport. The terms "mass transfer" and "mass transport" are used herein interchangeably. Mass transport refers to the rate in which a mass (e.g., a particle, a molecule, a substrate, or a nutrient) incorporates and/or diffuses into the living structure. In some embodiments, the particle diffuses into the living structure in at least about 10 seconds (s), about 15 s, about 20 s, about 30 s, about 40 s, about 50 s, or about 60 s upon initial contact with the particle. In some embodiments, the particle is in an aqueous, ionic, or organic solution. In some embodiments, the high mass transfer allows access of nutrients into the cells.

In some embodiments, the living structure has a customizable area. In some embodiments the living structure has a large area. A large area enables the living structures to be used for industrial scale reactions. In some embodiments, the living structure has an area of at least about 1 $cm^2$, about 10 $cm^2$, about 20 $cm^2$, about 30 $cm^2$, about 40 $cm^2$, about 50 $cm^2$, about 60 $cm^2$, about 70 $cm^2$, about 80 $cm^2$, about 90 $cm^2$, about 100 $cm^2$, about 110 $cm^2$, about 120 $cm^2$, about 130 $cm^2$, about 140 $cm^2$, about 150 $cm^2$, about 160 $cm^2$, about 170 $cm^2$, about 180 $cm^2$, about 190 $cm^2$, about 200 $cm^2$, about 210 $cm^2$, about 220 $cm^2$, about 230 $cm^2$, about 240 $cm^2$, about 250 $cm^2$, about 260 $cm^2$, about 270 $cm^2$, about 280 $cm^2$, about 290 $cm^2$, about 300 $cm^2$, about 310 $cm^2$, about 320 $cm^2$, about 330 $cm^2$, about 340 $cm^2$, about 350 $cm^2$, about 360 $cm^2$, about 370 $cm^2$, about 380 $cm^2$, about 390 $cm^2$, about 400 $cm^2$, about 410 $cm^2$, about 420 $cm^2$, about 430 $cm^2$, about 440 $cm^2$, about 450 $cm^2$, about 460 $cm^2$, about 470 $cm^2$, about 480 $cm^2$, about 490 $cm^2$, about 500 $cm^2$, about 510 $cm^2$, about 520 $cm^2$, about 530 $cm^2$, about 540 $cm^2$, about 550 $cm^2$, about 560 $cm^2$, about 570 $cm^2$, about 580 $cm^2$, about 590 $cm^2$, about 600 $cm^2$, about 610 $cm^2$, about 620 $cm^2$, about 630 $cm^2$, about 640 $cm^2$, about 650 $cm^2$, about 660 $cm^2$, about 670 $cm^2$, about 680 $cm^2$, about 690 $cm^2$, or about 700 $cm^2$. In some embodiments, the living structure has an area between about 10 cm² to about 700 cm², about 200 cm² to about 700 cm², about 500 cm² to about 700 cm², about 100 cm² to about 600 cm², about 30 cm² to about 210 cm², about 40 cm² to about 310 cm², about 50 cm² to about 500 cm², about 150 cm² to about 650 cm², or about 100 cm² to about 600 cm².

In some embodiments, the living structure has a customizable volume. In some embodiments the living structure has a large volume. In some embodiments, the living structure has a volume of at least about 10 cm³, about 20 cm³, about 30 cm³, about 40 cm³, about 50 cm³, about 60 cm³, about 70 cm³, about 80 cm³, about 90 cm³, about 100 cm³, about 110 cm³, about 120 cm³, about 130 cm³, about 140 cm³, about 150 cm³, about 160 cm³, about 170 cm³, about 180 cm³, about 190 cm³, about 200 cm³, about 210 cm³, about 220 cm³, about 230 cm³, about 240 cm³, about 250 cm³, about 260 cm³, about 270 cm³, about 280 cm³, about 290 cm³, about 300 cm³, about 310 cm³, about 320 cm³, about 330 cm³, about 340 cm³, about 350 cm³, about 360 cm³, about 370 cm³, about 380 cm³, about 390 cm³, about 400 cm³, about 410 cm³, about 420 cm³, about 430 cm³, about 440 cm³, about 450 cm³, about 460 cm³, about 470 cm³, about 480 cm³, about 490 cm³, about 500 cm³, about 510 cm³, about 520 cm³, about 530 cm³, about 540 cm³, about 550 cm³, about 560 cm³, about 570 cm³, about 580 cm³, about 590 cm³, about 600 cm³, about 610 cm³, about 620 cm³, about 630 cm³, about 640 cm³, about 650 cm³, about 660 cm³, about 670 cm³, about 680 cm³, about 690 cm³, or about 700 cm³. In some embodiments, the living structure has volume between about 10 cm³ to about 700 cm³, about 200 cm³ to about 700 cm³, about 500 cm³ to about 700 cm³, about 100 cm³ to about 600 cm³, about 30 cm³ to about 210 cm³, about 40 cm³ to about 310 cm³, about 50 cm³ to about 500 cm³, about 150 cm³ to about 650 cm³, about 1 cm³ to about 600 cm³, or about 100 cm³ to about 600 cm³.

In one embodiment, the living structure has one or more of the following characteristics: biocompatibility, large area of at least about 100 cm², a self-supporting 3D geometry, high resolution of at least about 50 µm, a high catalytic activity of at least about 10 g/L volumetric productive per 0.1 g bio-ink, metabolic activity and/or cell viability for at least about 2 months, high mass transport, tunable cell density and/or intercellular distance, or is catalytic. In another embodiment, the living structure has one or more of the following characteristics: biocompatibility, large area of at least about 225 cm², a self-supporting 3D geometry, high resolution of about 100 µm, a high catalytic activity of at least about 16 g/L volumetric productive per 0.1 g bio-ink, metabolic activity and/or cell viability for at least about 4 months, high mass transport, tunable cell density and/or intercellular distance, or is catalytic. In another embodiment, the living structures are made from the printing, extruding, and/or depositing of a bio-ink material comprised of freeze-dried cells of a single filler. In yet another embodiment, the living structure is made from printing, extruding, and/or depositing a bio-ink further comprised of a dual filler where the dual filler is cellulose.

In some embodiments, the method of making the living structure comprises printing, extruding and/or depositing the bio-ink. In some embodiments, the bio-ink is printed, extruded, and/or deposited on a surface. In some embodiments, the living structure is a printed living structure.

In some embodiments, the method of making the living structure uses a direct writing technique, which eliminates the need for additional and/or expensive equipment and tools such as dyes, lasers, and lithographic masks. Direct writing techniques provide control of the bio-ink composition, rheological behavior and printing parameters and can enable the printing of structures spanning a wide range of geometries. In various embodiments, the direct writing technique includes filamentary-based printing techniques, robotic deposition, micropen writing, fused deposition, droplet-based printing techniques, or ink-jet printing. In some embodiments, once formed, the living structure is cured by the irradiation of light.

In some embodiments, the method of making the living structure comprises seeding at least one additional cell into the living structure. In another embodiment, the method eliminates and/or reduces the step of seeding an additional cell.

Methods of Using the Living Structure

Aspects of this disclosure are directed to the use of a living structure according to an embodiment disclosed and described herein for biosensing, tissue regeneration, environment sensing, drug discovery, catalysis, and/or clinical implementations.

In one embodiment, the living structure can be used for biosensing for biomedical and bioanalytical applications, including early detection and chronic management of illness, pathogen testing, toxicology assays, and drug screening. Biosensing refers to the ability of the living structure to detect changes and/or fluctuations in the surrounding biological environment.

In another embodiment, the living structure can be used in vitro and/or in vivo to detect at least one or more analytes. In some embodiments the one or more analytes is a pathogen, a protein, DNA, a toxin, an antibody, an antigen, and/or an enzyme. In yet another embodiment, the living structure can used in vitro to detect a biological analyte from a sample (e.g., blood, serum, or other body fluid), where the biological analyte is a chemical or a biomolecule such as a protein, peptide, oligonucleotide, and/or polysaccharide. In another embodiment, the living structure can detect multiple analytes.

In another embodiment, the living structure can be used for environment sensing. Environment sensing refers to the ability of the living structure to detect changes and/or fluctuations in environmental conditions such as temperature, humidity, volatile gas compounds (VOCs), particulate matter, and/or gas levels.

In some embodiments, the biosensor and environment sensor report the detected changes via a signal, wherein the signal can be for example, in the form of an analytical signal such as an optical (i.e., changes in light absorption), electrochemical (i.e., changes in the surround environment due to biological or chemical reactions), pyroelectric (i.e., changes in temperature that induce current), gravimetric (i.e., changes in mass), or piezoelectric (i.e., changes in pressure, temperature, or strain) signal.

In another embodiment, the living structure can be used for tissue regeneration. Tissue regeneration refers to a method of restoring, treating, and/or healing a lost, diseased, damaged, or wounded tissue. In some embodiments, the tissue regeneration is non-invasive or minimally invasive. In some embodiments the lost, diseased, damaged, or wounded tissue to be regenerated includes nerve, muscle tissue, liver, heart, lung, breast, bladder, thymus, and/or skin tissue. In some embodiments, the disclosure provides methods for obtaining a sample of a lost, diseased, damaged, and/or wounded tissue, extracting and freeze drying the cells, preparing a living structure in vitro, and implanting the living structure in vivo to repair and restore the tissue.

In another embodiment, the living structure can be used for drug discovery and/or drug screening. Drug discovery and/or screening involves the use of assays to identify therapies useful in treating and/or preventing a disease or condition in a subject. For example, in some embodiments, the methods include utilizing cells of a particular subject to engineer living structures in the form of tissues, disease models, and/or tumor models. In a further embodiment, the methods include applying a candidate therapeutic agent and/or therapy (e.g. radiation therapy, anticancer agent, antibiotic, analgesic, anti-inflammatory agent, or immunosuppressant) to the tissue or model; measuring viability of the cells; and selecting a therapeutic agent and/or therapy for the subject based on the measured viability of the cells. In some embodiments, the drug discovery and/or drug screening is useful in in a variety of therapeutic areas including infectious disease, hematology, oncology, pediatrics, cardiology, central nervous system disease, neurology, gastroenterology, hepatology, urology, infertility, ophthalmology, nephrology, orthopedics, pain control, psychiatry, pulmonology, vaccines, wound healing, physiology, pharmacology, dermatology, gene therapy, toxicology, and immunology. In some embodiments, the drug discovery and/or drug screening is applicable to population of subjects and/or an individual subject.

In another embodiment, the living structure can be used for catalysis. In another embodiment, the living structure can be used as a biocatalyst. In some embodiments, the methods including utilizing the living structure to catalyze a number of reactions including but not limited to, food fermentation, biofuel production, protein synthesis, wastewater treatment, and/or bioremediation. In another embodiment, as a biocatalyst, the living structure is useful in the pharmaceutical, food and beverage, chemical synthesis, waste management, and cosmetic industries. In another embodiment, the catalysis takes place in a bioreactor. In another embodiment, the living structure can carry out glucose fermentation (i.e., the conversion of glucose to ethanol and carbon dioxide ($CO_2$)). In another embodiment, the living structure is particularly useful for reactions that are limited by mass transfer and/or require a cell/liquid interface. In another embodiment, the living structure can encapsulate engineered cell strains to produce enzymes, biological therapeutics, vaccines, and recombinant proteins that are currently produce by industrial fermentation.

In another embodiment, the living structure can be used for clinical implementation. Clinical implementation refers to the use of the living structures for medical purposes such as surgical planning, implant design, or research and training models. In some embodiments of the invention, the living structure is useful in surgical planning, implant design, and/or research and training models by providing an anatomical model of a specific tissue and/or organ. The anatomical model can accurately represent the structure and pathology of the tissue and/or organ.

In some embodiments, for example, the methods include utilizing the living structures to model a tumor in an organ of a subject where the models provide an accurate identification the tumor location and environment, and then surgically removing the tumor from the organ. Accordingly, the living structure can provide a method for accurately simulating the organ, assessing surgical feasibility, and planning the best route for surgery (i.e., surgical planning). In another embodiment, the methods include utilizing the living structures to generate patient-specific implants, wherein the living structures can be printed in a wide range of customizable geometries that reflect specific organs and/or tissues.

In some embodiments, the living structure is a tissue and/or organ. Non-limiting examples of tissues include bone, neural, fibrous connective tissue including tendons and ligaments, cartilage, dura, pericardia, muscle, lung, heart valves, veins and arteries and other vasculature, dermis, adipose, and glandular tissues. Non-limiting examples of organs include heart, lung, liver, kidney, urinary bladder, brain, ear, eye, gallbladder, bone, and skin.

In some embodiments, the living structure simulates an in vivo cell environment. Simulation of an in vivo cell environment includes mimicking the morphology, intercellular interactions, signaling pathway activation, and/or diffusion of cells. Cell morphology refers to the shape, structure, form and size of the cells. Intercellular interactions refer to the direct cell to cell communication in response to changes in the environment. Signaling pathway activation refers to the process by which a chemical or physical signal is initiated and transmitted through cells. Diffusion refers to both the action and passive transport of ions, atomic, and molecular substances across the cell membrane. In some embodiments, the morphology, intercellular interactions, signaling pathway activation, and/or diffusion barriers of the cells in the living structure are the same as their source cells (e.g., bacteria, algal, fungi, and protozoa cells). In some embodiments, by mimicking the morphology, intercellular interactions, signaling pathway activation, and/or diffusion barriers of cells, the living structures can simulate the in vivo cell environment.

In some embodiments, the living structure can be used to make textiles. Non-limiting examples of textiles include fabric, cloth, woven fabric, flax, cotton, and/or hemp. In some embodiments the textiles are biodegradable. Biodegradable refers to a substance (i.e., a textile) that can be decomposed by bacteria, fungi, or other living organisms. It is contemplated that the use of living structures to make biodegradable textiles can reduce the waste streams and pollution associated with the production textiles (e.g, clothing).

The living structures disclosed and described herein are useful for one or more of the following biocatalysis, tissue engineering and regenerative medicine, biosensing, drug discovery, environment sensing, clinical implementation, or simulating an in vivo cell environment. In some embodiments, the living structures are useful in detecting fluctuations in the surrounding environment. In another embodiment, the living structure is useful in generation of anatomically accurate models of tissues and/or organs. In another embodiment, the living structure is useful for carrying out glucose fermentation.

EXAMPLES

Example 1: Microbe Bio-Ink Preparation

Bioprinting is a powerful fabrication technology to create complex 3D scaffolds that contain living cells and has been demonstrated for applications ranging from biosensing, tissue regeneration, environment sensing, drug discovery and clinical implementation. Key to the success of bioprinting applications is the development of an ink material, or a "bio-ink", which integrates living cells into a printable ink that can be further fabricated into customized 3D geometries. To ensure cell viability and activity, the ink composition and printing process must be biocompatible and the printed structures should be permeable to ensure cellular nutrient acquisition.

The bio-ink was prepared by mixing nanocellulose crystal powder (The university of Maine, Process development center, Orono, Maine) and/or freeze-dried Baker's yeast granules (Fleischmann's RapidRise® Instant Yeast, Fleischmann Inc., St. Louis, MO) of appropriate weight. Use of nanocellulose crystalline powder enabled control of cell density. Lithium phenyl-2,4,6-trimethylbenzoylphosphinate (LAP) is a photo-initiator that enabled photo-curing at a wavelength of 405 nm. It is contemplated that photo-curing at a higher wavelength may lead to decreased UV damage of the cells as compared to a photo-initiator such as Irgacure, which is primarily used at 365 nm (i.e., higher energy).

Figure 2:
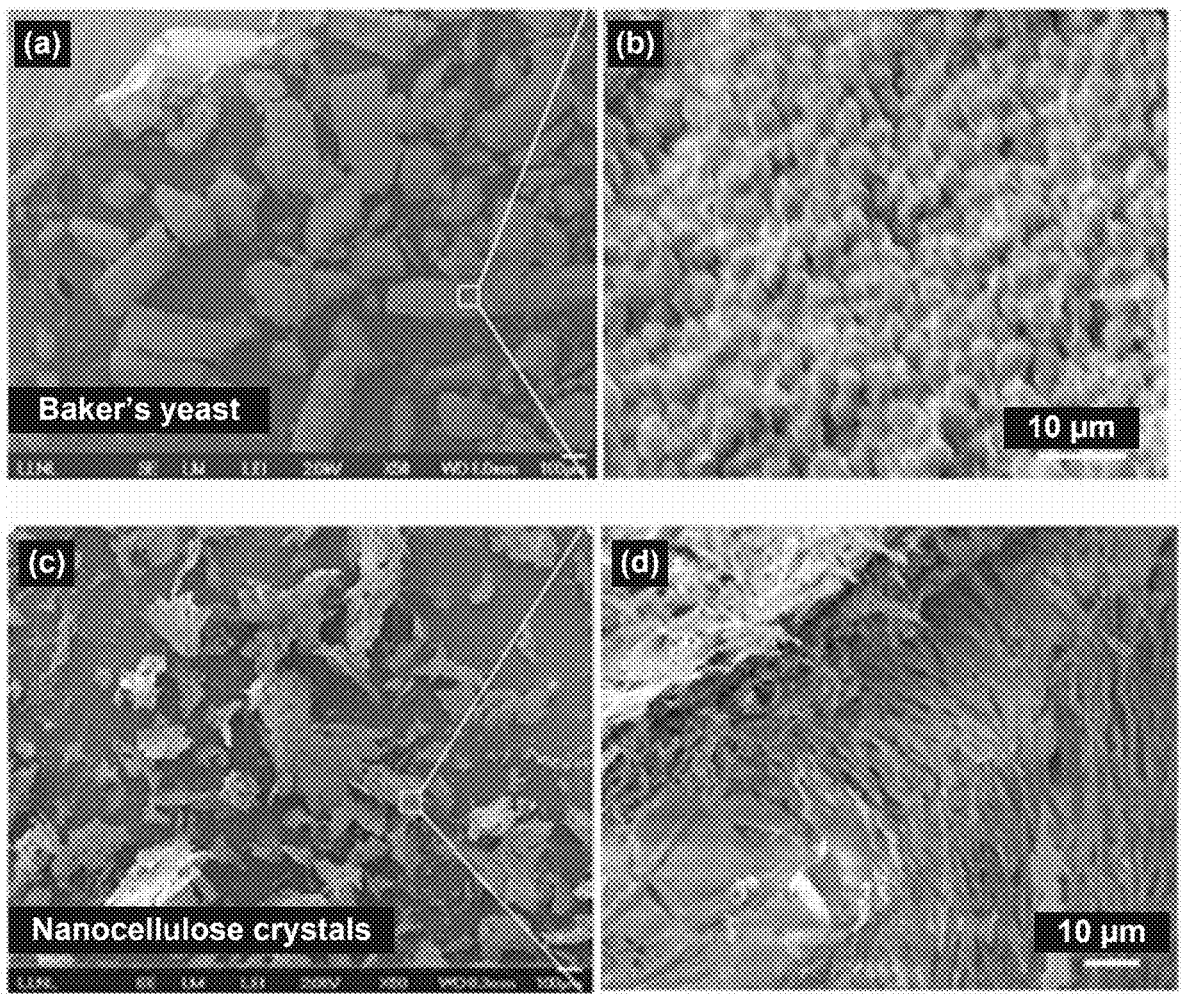
FIG. 2A and FIG. 2B are representative scanning electron microcopy (SEM) images of yeast granules.
FIG. 2C and FIG. 2D are representative SEM images of nanocellulose crystalline powder.
Figure 3A:
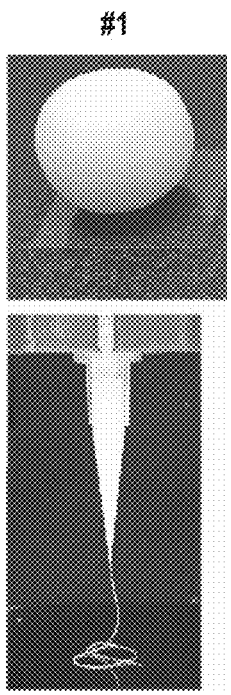
FIGS. 3A-3E depict representative photographs of various geometries and extrusions of bio-ink doughs.
Figure 3B:
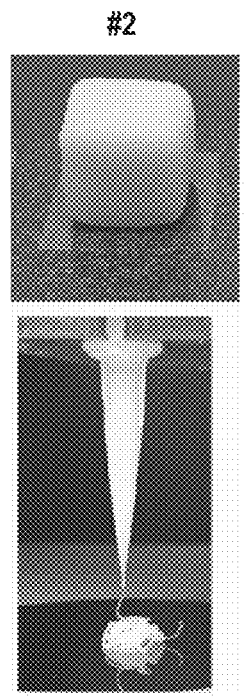
Figure 3C:
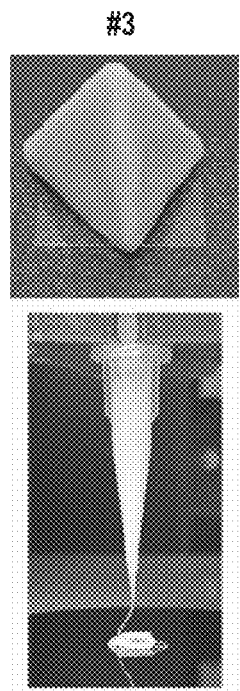
Figure 3D:
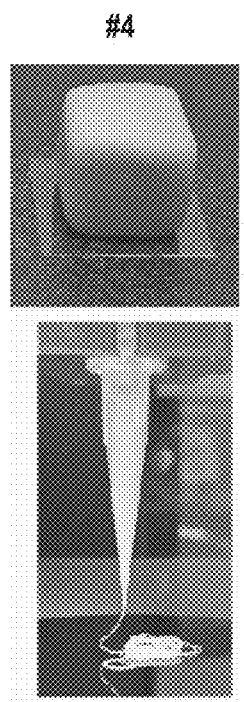
Figure 3E:
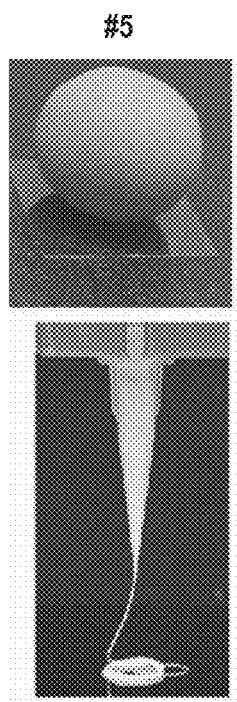

FIG. 1A depicts the three-component system where the filler(s) are freeze-dried yeast granules and/or freeze-dried nanocellulose crystalline powder, the binder is polyethylene glycol dimethacrylate (PEGDA), and the photo-initiator is LAP. Sterile phosphate-buffered saline (PBS) solution (Teknova Inc., Hollister, CA) containing 10 wt % of PEGDA (i.e., the binder) and 0.01 wt % of LAP (Sigma-Aldrich, St. Louis, MO) (i.e., the photo-initiator) was mixed with the pre-weighed fillers until a dough-like consistency of the bio-ink was formed. The bio-ink was then loaded into a 5-mL syringe barrel and placed on ice prior to printing. FIG. 1B is a photograph of the printer using the bio-ink to print a 3D structure. FIGS. 2A and 2B are scanning electron microscopy (SEM) images of the yeast granules consisting of close-packed cells with an ovoid shape and an average size of 3 μm prior to preparing the bio-ink. FIGS. 2C and 2D are SEM images of the nanocellulose crystal powered consisting of nanofibrous structures prior to preparing the bio-ink.

Table 1 below shows the formula of five representative inks with systematically increased yeast-to-nanocellulose weight ratio (Y/N ratio) from 0 to 1, with cell loading from 0% to 42.8 wt %.

TABLE 1

Representative bio-ink formulas with varying concentration of yeast granules and nanocellulose crystalline powder

| Components | Ink #1 | Ink #2 | Ink #3 | Ink #4 | Ink #5 |
| --- | --- | --- | --- | --- | --- |
| Yeast (Y) | 0 | 0.6 g | 1.3 g | 2.8 g | 30 g |
| Nanocellulose (N) | 36 g | 34.4 g | 33.2 g | 28.0 g | 0 |
| PBS | 36 g | 34.4 g | 33.2 g | 28.0 g | 36 g |
| PEGDA | 4 g | 4 g | 4 g | 4 g | 4 g |
| LAP | 4 mg | 4 mg | 4 mg | 4 mg | 4 mg |
| Y/N Ratio | 0:1 | 1:60 | 1:25 | 1:10 | 1:0 |
| Cell Loading | 0 wt % | 0.8 wt % | 1.7 wt % | 4.0 wt % | 42.8 wt % |
| # of cells per cm$^3$ | 0 | $1.6 \times 10^8$ | $3.4 \times 10^8$ | $8.0 \times 10^8$ | $8.6 \times 10^9$ |
| Cell vol. density | 0 | 1.4 vol % | 2.9 vol % | 7.0 vol % | 75 vol % |

Each gram of Baker's yeast granules contains approximately 20 billion cells, as such, the volume of a single yeast cell is about 50 μm$^3$. Therefore, the cell density of bio-ink #5 (i.e., pure yeast ink) was estimated to be $8.6 \times 10^9$ cells/cm$^3$, or a volumetric ratio of 75 vol %. This cell concentration is significantly higher than a liquid culture of yeast cells grown under similar batch conditions (i.e., 2 wt % glucose) where the typical cell density is approximately 107 cells/cm$^3$ or a volumetric ratio of 0.05 vol %.

FIGS. 3A-3E (top panel, labeled #1-5) show the various geometries of bio-ink doughs molded by hand corresponding to the bio-inks enumerated in Table 1. Rather than appearing as viscous liquid and/or gels as conventional bio-inks, FIGS. 3A-3E (top panel) show that presently disclosed bio-inks have solid shapes. However, as shown in FIGS. 3A-3E (bottom panels) the solid shapes can be easily liquefied in the presence of shear stress when extruded from a nozzle. This observation indicates the presently disclosed bio-inks are viscoelastic materials with well-suited rheological behavior and shear-thinning properties. Compared to other bio-inks such as alginate, the bio-ink material is more robust, more resistant to biodegradation and can enable higher printing resolution.

Figure 4:
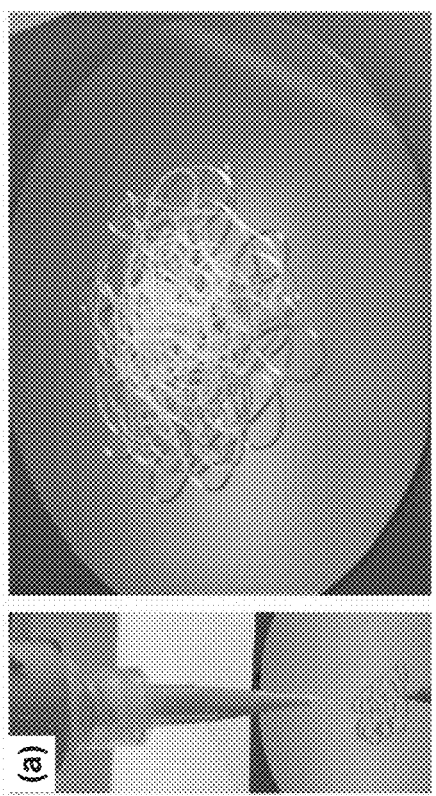
FIGS. 4A and 4B are representative photographs of the extrusion of bio-inks comprised of yeast granules and nanocellulose crystalline powder, respectively.
Figure 4:
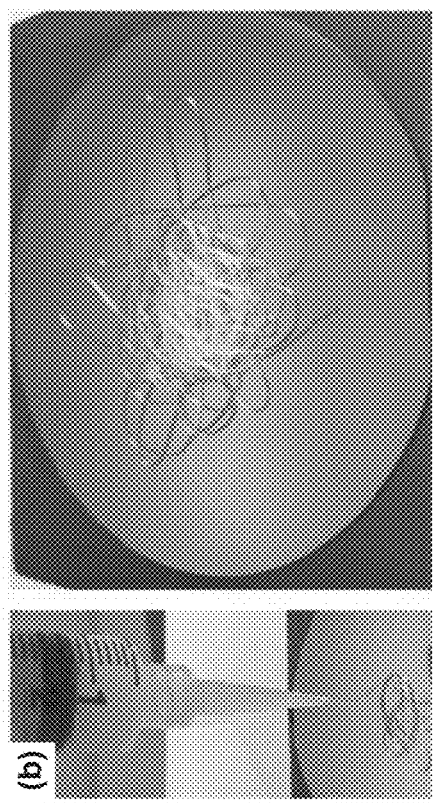

FIGS. 4A and 4B depict additional extruded exemplary bio-inks comprised of only yeast and only nanocellulose crystalline powder with the formulas enumerated in Table 2.

TABLE 2

Representative bio-ink formulas comprised of only yeast granules and only nanocellulose crystalline powder.

| Components | Yeast Ink | Nanocellulose Ink |
| --- | --- | --- |
| Yeast | 3 g | 2 g |
| PBS | 3.6 g | 3.6 g |
| PEGDA | 4 g | 4 g |
| LAP | 4 mg | 4 mg |

Figure 5:
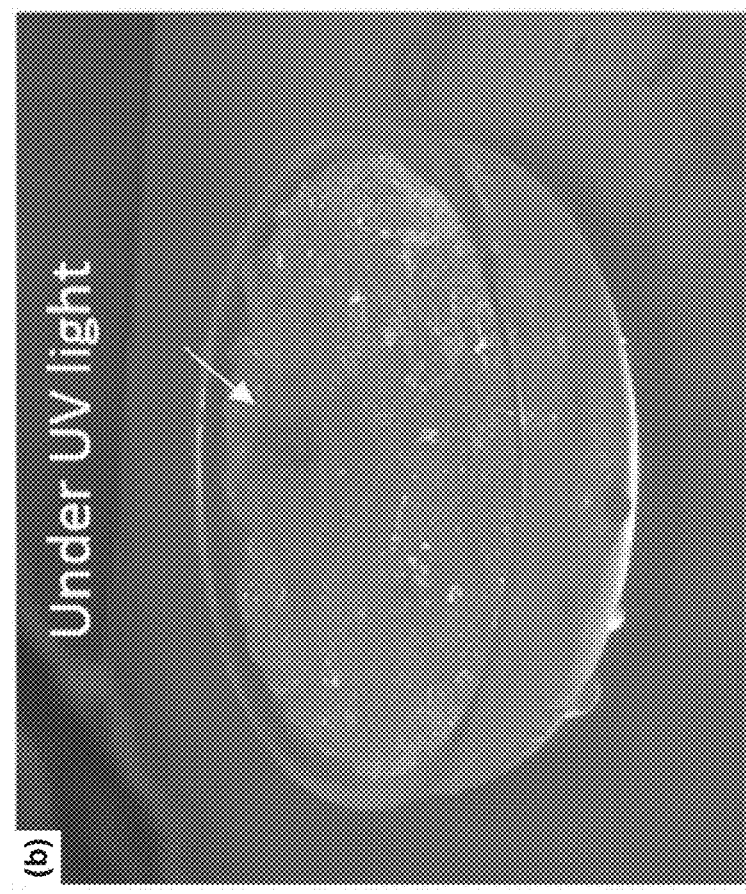
FIGS. 5A and 5B are representative photographs of extruded and cured bio-ink.
Figure 5:
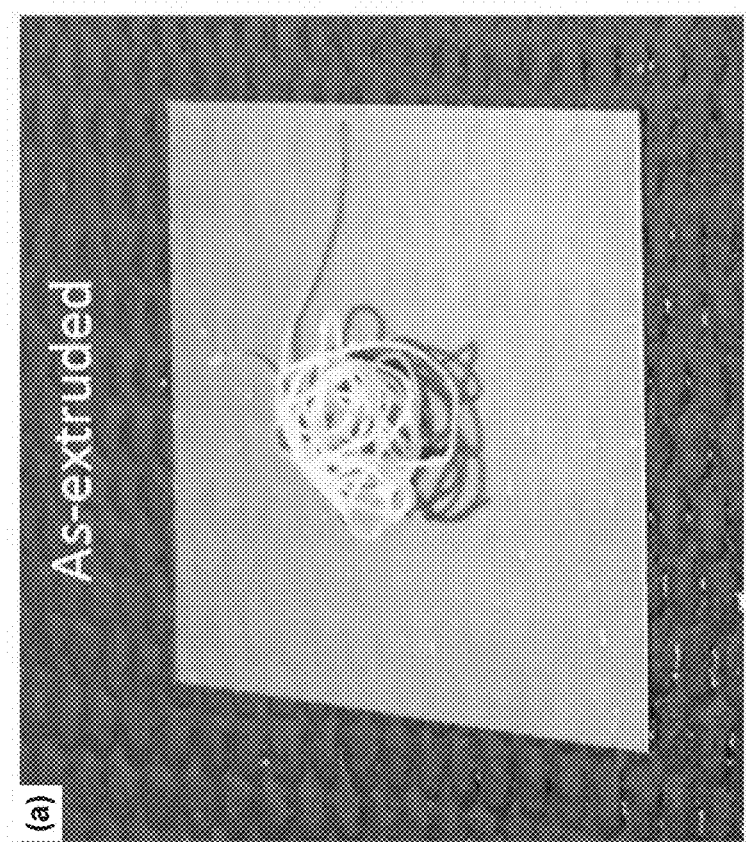
Figure 6:
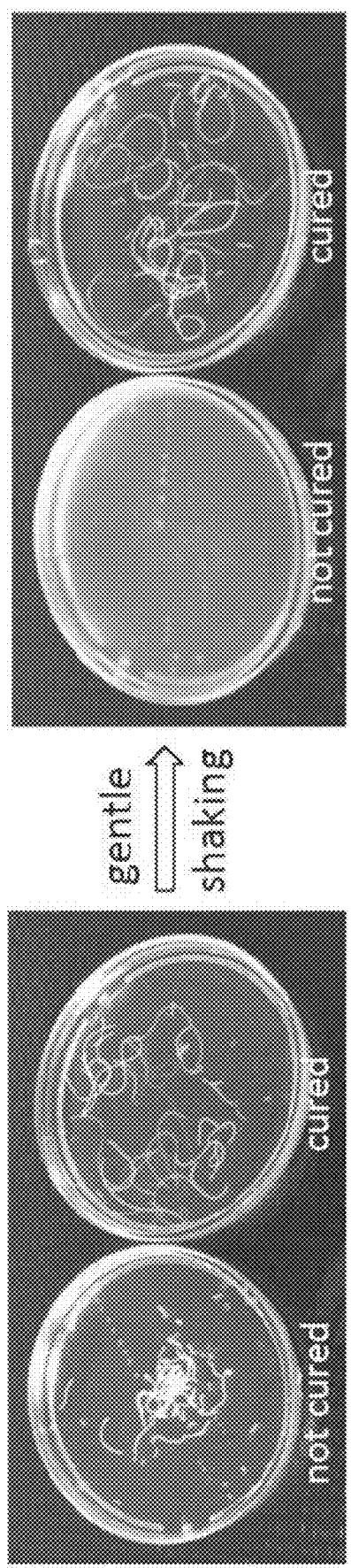
FIG. 6 is a representative photograph of cured and uncured extruded bio-inks.

Once extruded, the bio-inks can be photo-crosslinked via curing under a light emitting diode (LED) illumination at a wavelength of 405 nm as shown in FIGS. 5A and 5B. The extruded bio-ink was illuminated for 10 sec and placed on ice to reduce dehydration. FIGS. 5A and 5B depict the extruded ink before and during LED illumination. FIG. 6 is a comparative image of a bio-ink that has not been photo-crosslinked (i.e., not cured) and of a bio-ink that has been photo-crosslinked (i.e., cured) soaked in a PBS solution. Importantly, upon gentle shaking, the bio-ink that has not been photo-crosslinked does not maintain its structure whereas the photo-crosslinked bio-ink does.

Figure 7:
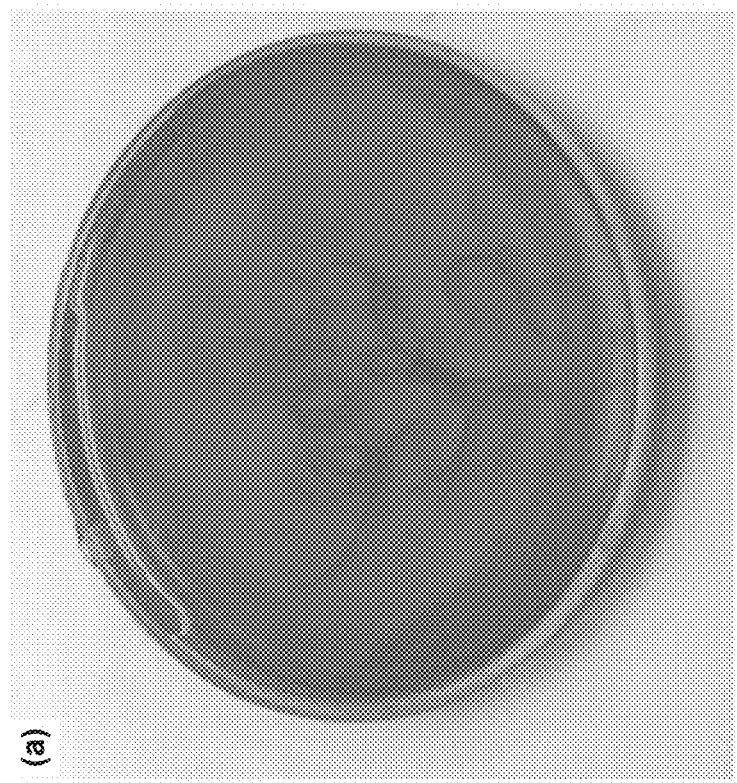
FIGS. 7A and 7B are representative photographs of stained, extruded bio-inks for demonstrating mass transfer.
Figure 7:

The extruded bio-ink can then be soaked in red food dye as depicted in FIGS. 7A and 7B. Once placed in the red food dye, the extruded bio-ink turned red within a minute. Notably, the yeast only bio-ink absorbed the red dye more quickly than the nanocellulose only bio-ink, which indicates that the introduction of yeast to the bio-inks facilitates a faster mass transport.

Example 2: Rheology of Bio-inks

A general challenge for extrusion-based printing is the tailoring of ink compositions to achieve required rheology to enable reliable flow through fine nozzles and maintenance of shape integrity after deposition. For inks that use a solid filler to tune rheology, the loading plays a critical role in determining the printability. In particular, if the loading is too low, the printed shape is too soft to maintain the geometry however, if the loading is too high, the ink can be too stiff to be extruded and limit feature resolution.

Figure 8:
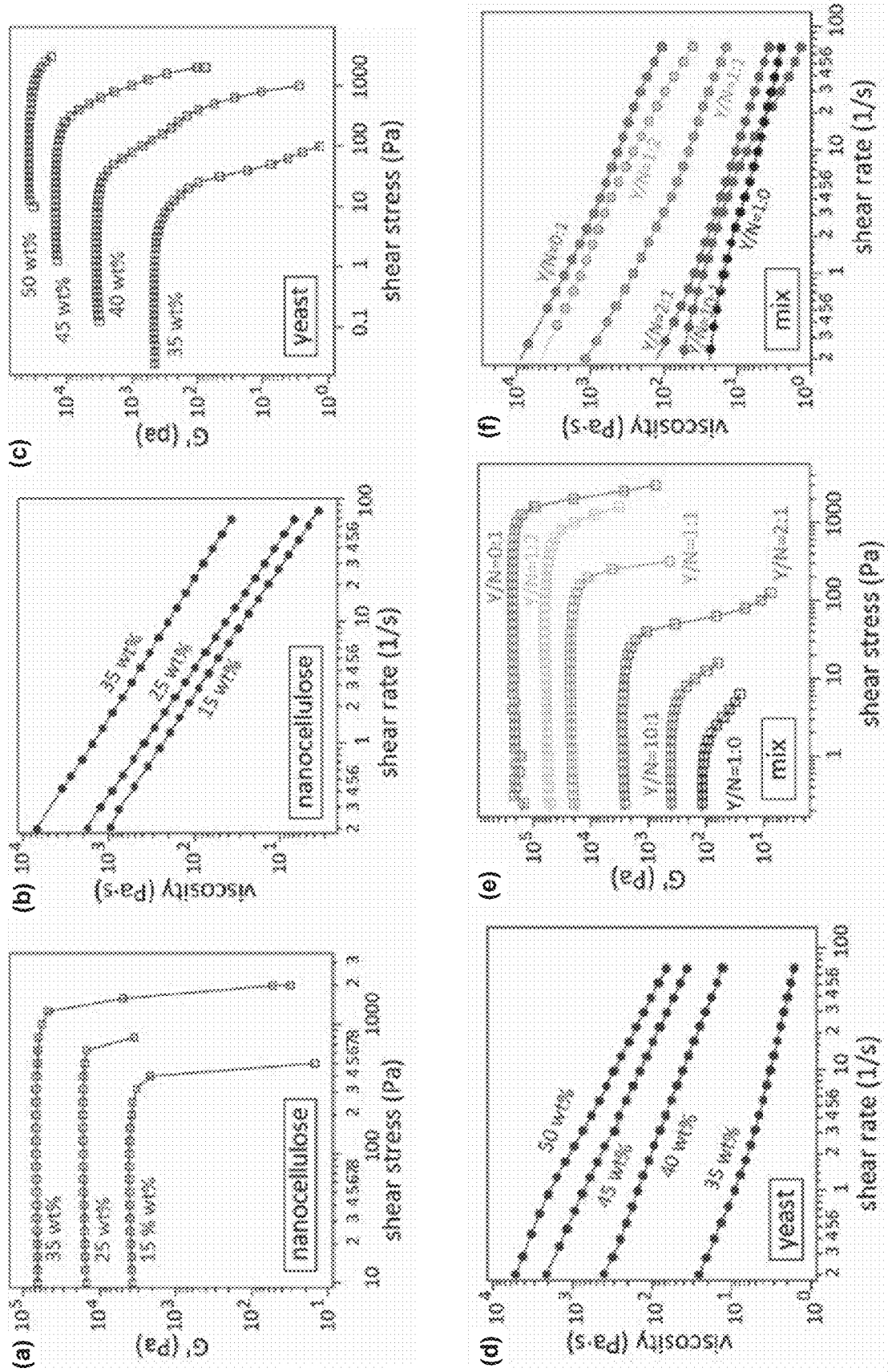
FIGS. 8A-8F are representative graphs of rheological data from bio-inks comprised of nanocellulose crystalline powder, yeast granules, or a composite of nanocellulose crystalline powder and yeast granules.

To obtain comprehensive knowledge of the bio-ink with single and dual-fillers, systematic studies of ink rheology were conducted as a function of loading and ratio of the two fillers (i.e., yeast granules and/or nanocellulose crystalline powder) as shown in FIG. 8.

Shear flow and shear elastic modulus were measured for yeast granules and nanocellulose crystalline powder bio-inks using a stress-controlled rheometer (AR 2000ex, TA Instruments Inc., New Castle, DE) with a 40-mm$^2$-degree-cone geometry and a gap of 500 μm. A solvent trap apparatus consisting of a water reservoir and cover plate were used to minimize evaporation from the sample during the experiment. After loading the bio-inks into the measuring system, a pre-shearing of 1 second(s)$^{-1}$ for a period of 60 s and a following equilibration (zero shear rate rest) time of 60 s were applied prior to each measurement. The apparent viscosity of the bio-ink was measured as a function of increasing shear rate (0.01-100 s$^{-1}$ at 20 discrete value points with logarithmic spacing). An equilibration time of 30 s was observed at each value of desired shear rate prior to reading the shear stress. Oscillation measurements were performed at a frequency of 1 Hz to detect the elastic (G') and viscous (G") moduli, while an ascending stress sweep (1-1000 Pa) was applied with logarithmic spacing. Again, a 30 s equilibration was observed prior to recording the complex modulus data. The results report only G'. All measurements were carried out at a constant temperature of 20° C.

FIG. 8A shows that the pure nanocellulose bio-inks are printable when loading is between about 10 to 40 wt %. The addition of nanocellulose caused the plateau modulus ($G_{eq}'$) of the bio-ink to increase drastically from only a shear stress of approximately 3,500 (15 wt %) to over 60,000 Pascals (Pa) elastic (35 wt %). Further, FIG. 8B shows that the 35 wt % nanocellulose bio-ink had an order of magnitude higher apparent viscosity than that of the 15 wt % bio-ink. In contrast, the pure yeast granule bio-inks are printable when the loading is between about 30 to 50 wt %. Similarly, FIG. 8C shows that when the cell concentration was increased from 35 to 50 wt %, the yeast only bio-ink's $G_{eq}'$ displayed a dramatic increase from approximately 400 to approximately 40,000 Pa. In addition, FIG. 8D shows the shear flow curves exhibited almost the same negative slopes as the pure nanocellulose bio-inks. These rheological values confirm that both yeast granules and nanocellulose fillers can act as a viscosifier to generate a liquid-to-solid transition by imparting a yield stress to the precursor suspension. Since either component (i.e., yeast granules or nanocellulose crystalline powder) yielded bio-inks with excellent shear-thinning behavior, the composite bio-ink (i.e., the bio-ink consisting of both yeast granules and nanocellulose crystalline powder) provided a full spectrum of printability regardless of the yeast granules to nanocellulose crystalline powder ratio.

For example, keeping the total solid loading of the bio-inks at about 33 wt % while tuning the Y/N ratio from 1:0 to 0:1 (See formulas shown in Table 1), the $G_{eq}'$ of the composite bio-inks as shown in FIG. 8E varied across three orders of magnitude as the Y/N ratio changed. Further, FIG. 8F demonstrates that these composite bio-inks showed strong thixotropic properties as their apparent viscosities decreased with shear rates. The magnitudes of the key rheological parameters of the bio-ink presented in FIG. 8E are in agreement with those reported for other soft biomaterial-based inks designed for a 3D filamentary printing technique, such as hydrogels ($G_{eq}'$~100-3000 Pa, $\eta_0$~200-5000 Pa·s), silk fibroins ($G_{eq}'$~1 Pa, $\eta_0$~3 Pa·s), cellulose nanocrystals ($G_{eq}'$~300000 Pa, $\eta_0$~100000 Pa·s), and copolymers ($G_{eq}'$~10000 Pa, $\eta_0$~2000 Pa·s). Accordingly, the unique dual-filler formula of yeast granules and nanocellulose crystalline powder can provide bio-inks with tunable cell densities, mechanical stiffness, and rheological properties over a wide range.

Example 3: Fabrication of 3D Structures

A variety of 3D structures were fabricated using the bio-inks to include mesoscale periodic lattices, radial arrays, and other testing structures using a robotic deposition apparatus (Hyrel System 30M 3D printer). The robotic deposition apparatus provides an ink writing technique with an ink delivery system mounted on a x-y-z-axis motion gantry for agile printing onto a stage. Three-axis motion was independently controlled by a custom-designed, computer-aided direct-write program that allowed for the construction of complex, 3D architectures in a layer-wise deposition scheme.

The bio-ink was then dispensed by mechanically displacing the plunger on the bio-ink reservoir (i.e., the 5 mL syringe) at a pressure required to maintain the desired flow conditions and depositing the bio-ink onto a silicon wafer to print programmed 3D structures. Typically, the bio-ink, housed in a 5 mL syringe, was deposited as a continuous filament through a 200 μM cylindrical nozzle at a uniform volumetric flow rate of XX-YY and at a writing speed of 5-10 mm/s.

Immediately after printing, the structures were photo-cured by soaking the structures in a yeast peptone dextrose (YPD) medium containing 2 wt % glucose. They were cured under flood UV illumination (Loctite® LED Flood System, Henkel Corporation, Rocky Hill) with the irradiance of 400 mW/cm$^2$ at 405 nm for 10 s, then soaked in the YPD medium. For bulk samples, bio-ink material was sandwiched between two glass slides spaced by a 1.5-mm-thick silicone sheet. The bulk bio-ink layer was then cured under the UV illumination for 10 s, followed by soaking in the YPD medium.

Figure 9:
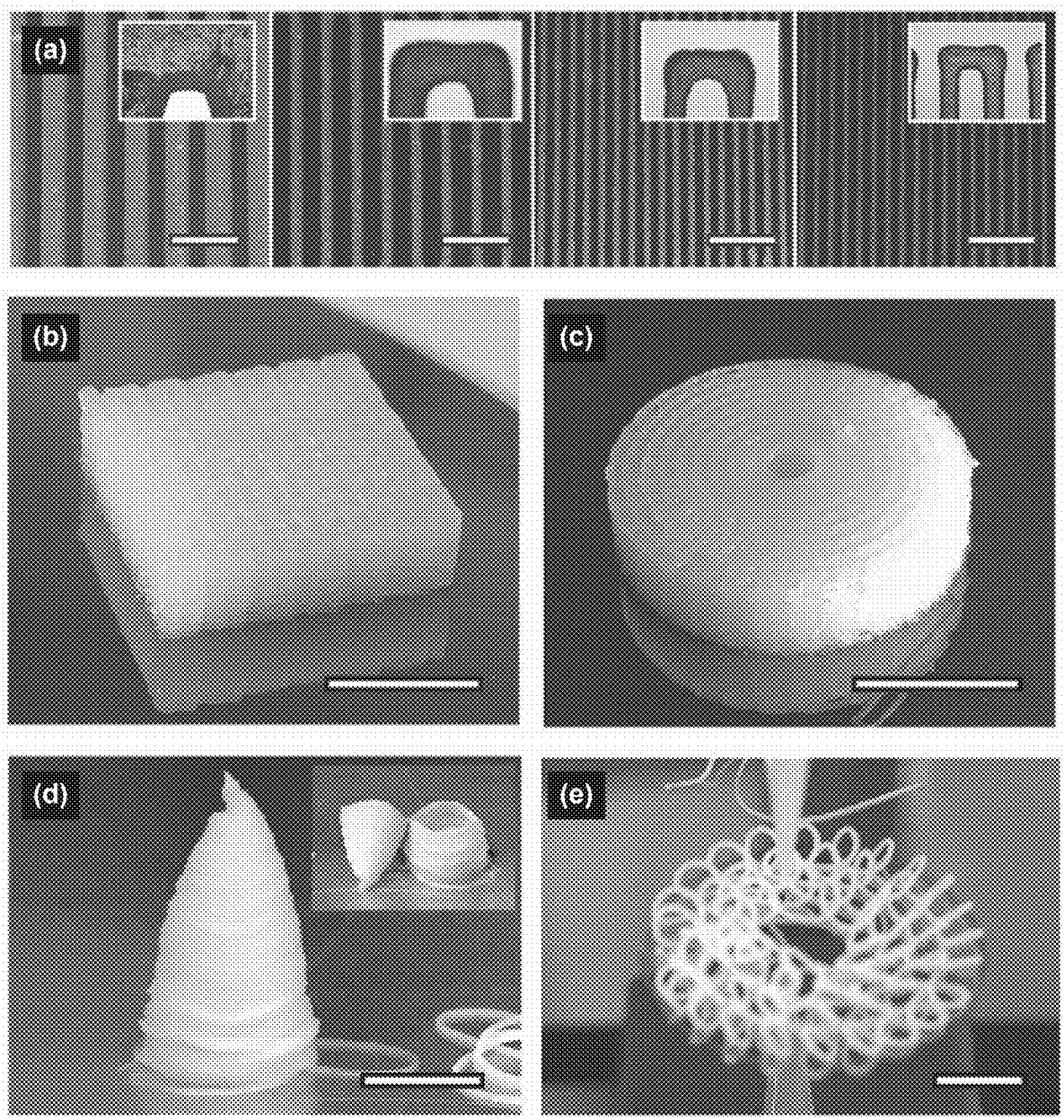
FIG. 9A are representative photographs and optical microscope images of printed bio-inks on a silicon surface.
FIGS. 9B-9E are representative photographs of 3D printed structures with various geometries.

As ink rheology determines the resolution and complexity of printable 3D geometries, two-dimensional serpentine patterns of the bio-ink were printed with decreasing nozzle sizes. FIG. 9A shows the photographs and optical microscope images of the printed structures using nozzle sizes of 1.6, 0.8, 0.5 and 0.2 mm, respectively (scale bars 5 mm). The printed filaments have uniform thicknesses across the whole pattern, consistent with the nozzle size. In addition, inhomogeneous "flakes" and a certain degree of surface roughness was observed in the inks containing nanocellulose crystalline powder. However, these "flakes" did not affect extrusion, and upon further investigation were found to be aggregates of insufficiently hydrated nanocellulose. If using yeast granules bio-inks, structures with extremely fine, 100-μm features can be printed. The extreme fineness of the lines did not favor the cell viability due to rapid drying, therefore nozzles of 200 μm or greater were used for printing in subsequent experiments.

FIGS. 9B-9E show 3D-printed structures with increasing complexity (scale bars 5 mm). FIGS. 9B and 9C depict micro-periodic geometries of simple-cubic and cylindrical scaffolds produced using repeated printing in-plane patterns while gradually lifting the nozzle up. More specifically, the cuboid lattices were produced with an in-plane center-to-center filament spacing (L) of 0.6 mm and a filament diameter (d) of 0.2 mm, resulting in a spacing-to-diameter ratio (L/d) of 3. In contrast, the cylindrical lattices were assembled by printing concentric circles in one x-y layer and with radial rods patterned in the adjacent layers with inner radii of 2 mm and outer radii of 10 mm. In these structures, each filament is partially supported from its underlying layer and therefore can tolerate "soft" inks, however this can also limit geometric flexibility.

Due to the excellent rheological properties of the bio-inks, unconventional 3D architectures can be printed such as the hollow cone or a circular translating coil structure (assisted by the viscous thread instability effect) as depicted in FIGS. 9D and 9E. The hollow cone structures were printed by stacking concentric circles with a gradually decreasing diameter and circular translating coil structures were printed with the assistance of the viscous thread instability effect. The hollow cone and circular translating coil architectures shown in FIGS. 9D and 9E have ultrahigh tensile strength, excellent self-supporting properties of the bio-inks, and are a demonstration of the manufacture of highly complex architectures that are very challenging to fabricate in extrusion-based printing techniques.

Example 4: Cell Culture and Viability

The biocompatibility of bio-ink composition and fabrication process were examined by live and/or dead cell viability assays and fluorescent microscopy. In preparation, the yeast cells of the bio-ink material were freeze-dried and not pre-cultured. After printing and curing, fabricated structures, with a high cell loading, were soaked in Difco™ Potato Dextrose Broth containing 2 wt % glucose and 0.4 wt % potato starch (BD Biosciences, San Jose, CA) at room temperature and the media were exchanged once every day.

The fabricated printed structures were stained using LIVE/DEAD™ BacLight™ Bacterial Viability Kit for microscopy & quantitative assays (Thermo Fisher Scientific Inc., Waltham, MA) which contained component A (SYTO 9 dye, 3.34 mM) and component B (propidium iodide, 20 mM). 3 µL of component A and 3 µL of component B were mixed thoroughly, followed by adding and subsequently mixing a 2 mL PBS solution to produce a staining solution. Printed lattices were soaked in the staining solution in the dark at room temperature for 30 minutes. To stain the cells, freeze-dried yeast granules were first dissolved and suspended in PBS solution, then a 3 µL aliquot of the dye mixture was added for every 1 mL of suspension. Staining was carried out in the dark at room temperature for 15 minutes.

Figure 10:
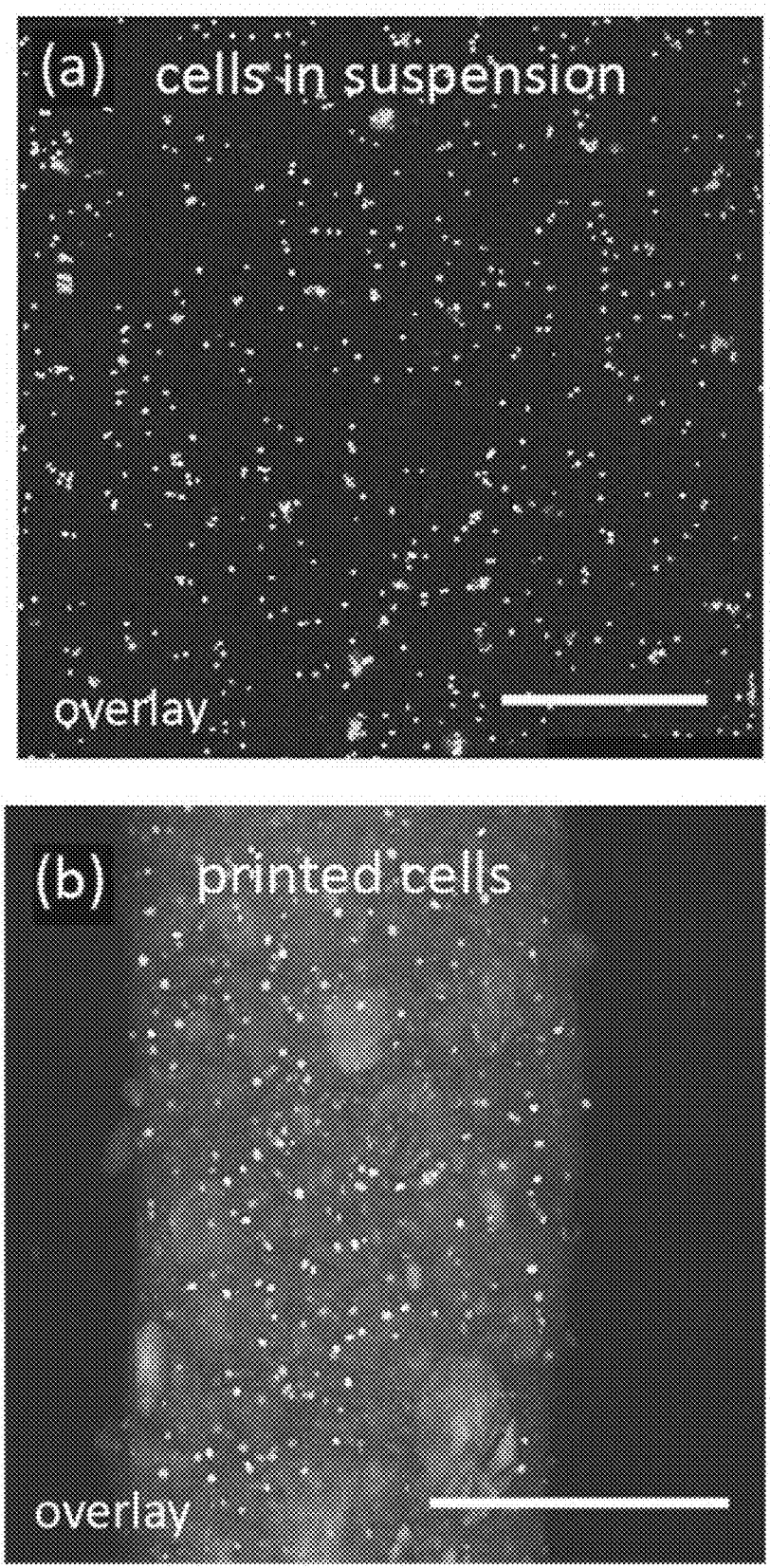
FIGS. 10A and 10B are representative confocal images of live-dead cell viability assays.

Confocal images were taken with a Leica SP5 laser scanning confocal microscope and a dry 10×/0.3 NA, 20×/0.75 NA or 40×/0.75 objective. Images were processed and analyzed by ImageJ/FIJI for overlay and cell counting. FIGS. 10A and 10B are confocal images of the cell suspension of freeze-dried cells and 200 µm thick filament of a printed lattice using the same freeze-dried cells (scale bars are 200 µm). The images indicate that cell viability of printed lattice and cell suspension were similar (31.4% and 35.9%, respectively). This similarity suggests that cell viability was determined primarily by the original dry granules used and not by the ink preparation and fabrication processes. Consistent with the observation of inhomogeneity under an optical microscope as depicted in the inset of FIG. 9A, patches with variable sizes ranging from several to several ten microns were observed inside the hydrogel filament. These patches did not contain cells and were believed to be nanocellulose segregates.

Figure 11:
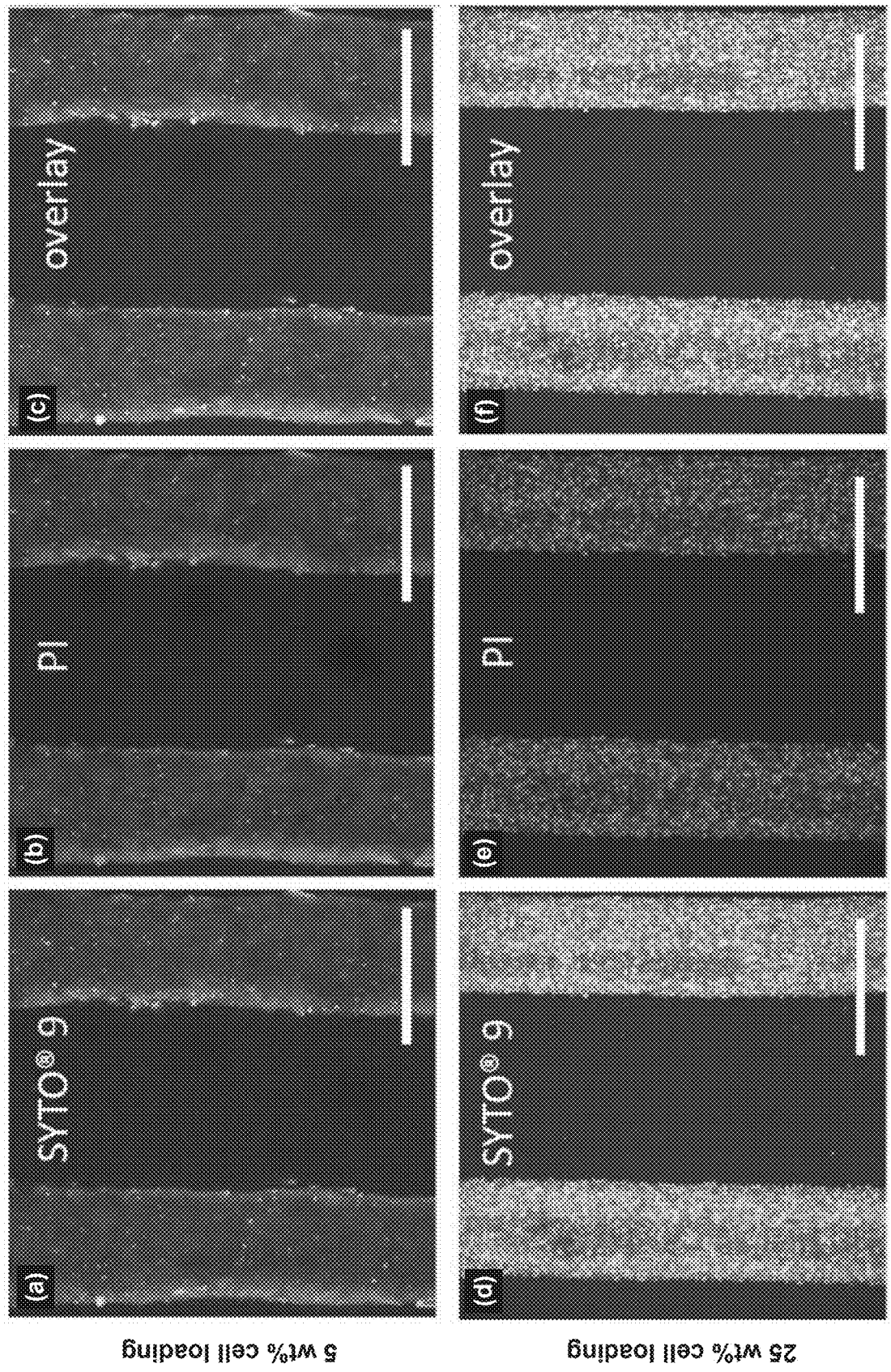
FIGS. 11A-11F are representative confocal images of printed structures with various cell loadings.
Figure 12:
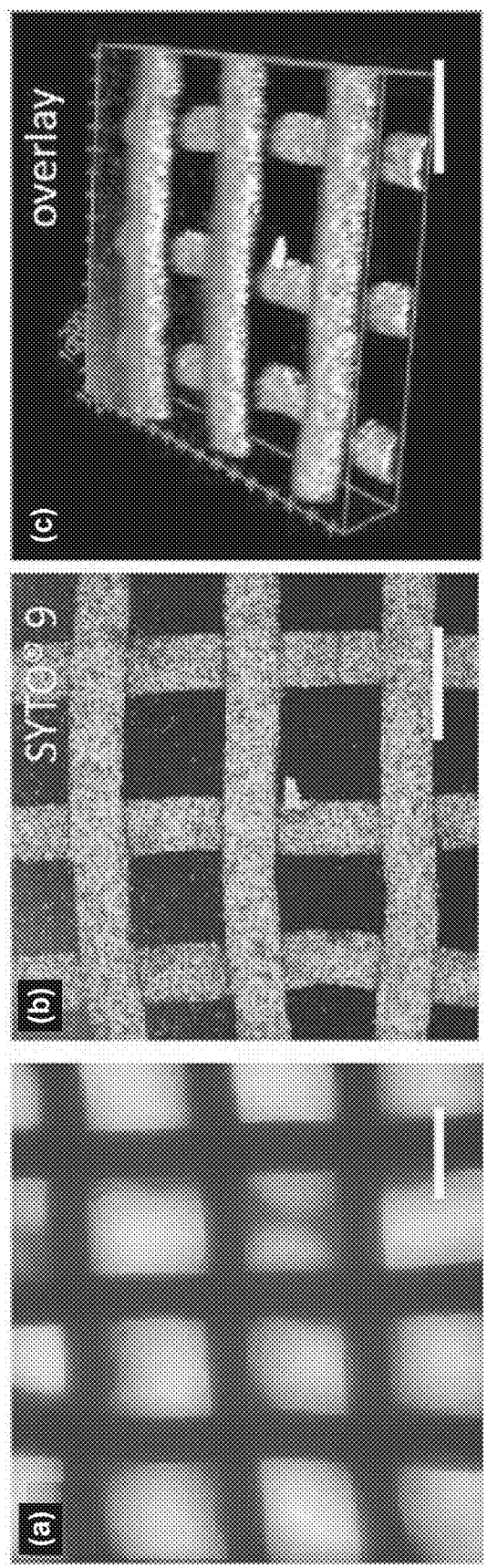
FIGS. 12A-12C are representative bright-field optical microscope images of a stained printed structure for the cell viability assays.
Figure 13:
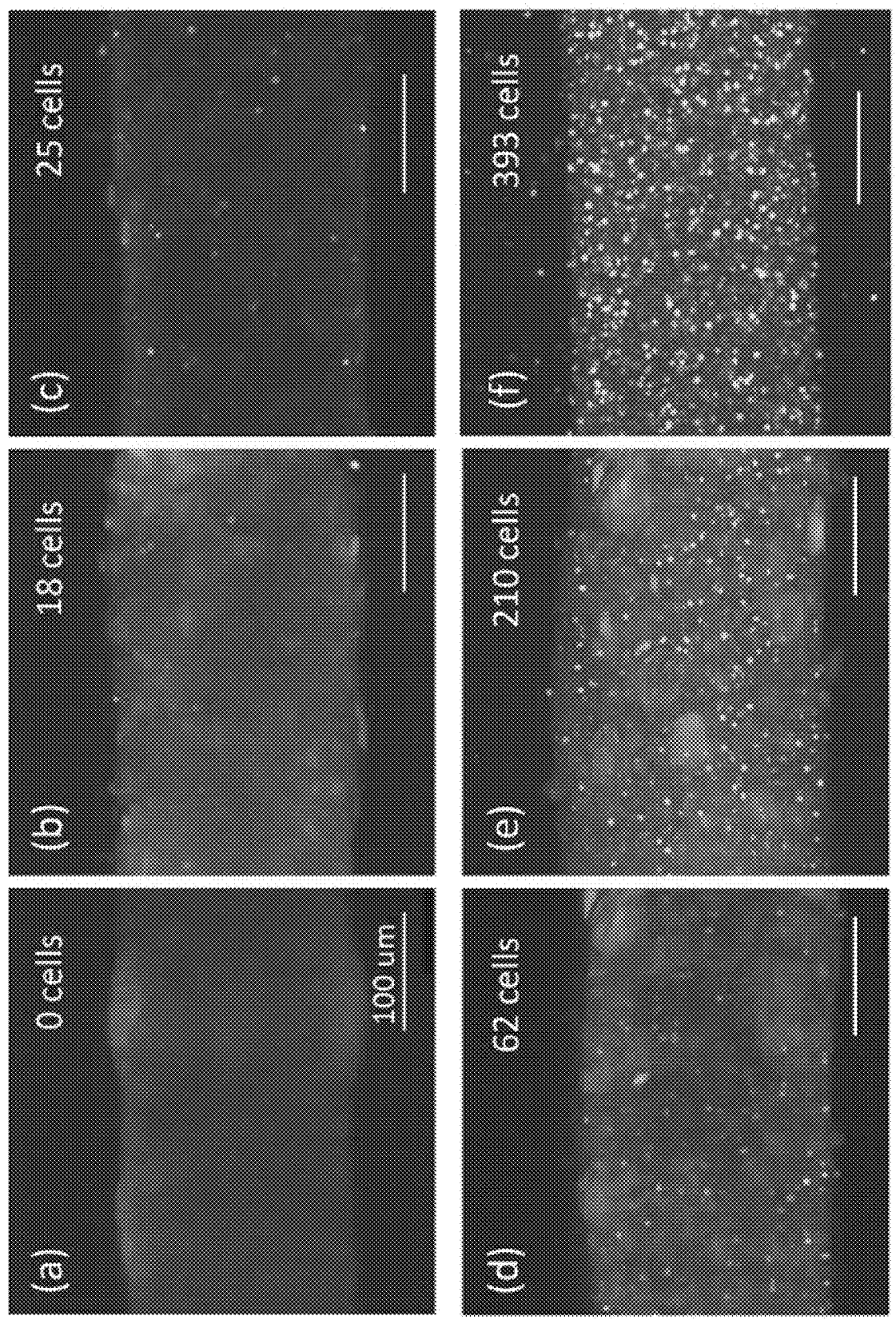
FIGS. 13A-13F are representative confocal images of printed structures with various cell densities and intercellular distances.

The impact of the bio-ink composition on the resulting cell viability was studied on two distinct ink compositions. FIGS. 11A-11C and FIGS. 11D-11F are confocal images of the printed scaffolds with a 5.5 wt % cell loading and 24.6% wt % of nanocellulose, respectively (scale bars are 250 µm). FIGS. 11A and 11D are of cells were stained with SYTO®9), FIGS. 11B and 11D are stained with propidium iodide, and FIGS. 11C and 11F are an overlay of FIGS. 11A and 11B and FIGS. 11D and 11E, respectively. Scale bars are 250 µm. FIG. 12A is bright-field optical microscope image, FIG. 12B is a confocal top-view image, and FIG. 12C is a reconstructed microscope image of the stained, printed lattice with a cell loading of 23.4 wt % and nanocellulose loading of 11.6 wt % (scale bars are 500 µm). FIGS. 11C, 11F, and 12C marked with overlay in the top right corner depict both live and dead/damaged cells. Importantly, regardless of loading, both viable and dead/damaged cells were well-dispersed in the printed structures in all three dimensions.

Example 5: Cell Density and Intercellular Distance

To assess whether tunability of the cell loading during bio-ink preparation allows for rational control over cell densities and intercellular distance, six printed lattices with varying concentrations of cell loading and nanocellulose crystalline powder were prepared. FIGS. 13A-13F show laser-scanning confocal microscope images of the six printed lattices with an increasing cell loading of 0, 0.6, 2.4, 5.5, 12.3, 23.4 wt % and a decreasing nanocellulose loading of 28.6, 28.2, 26.8, 24.6, 19.7, 11.6 wt %, respectively (scale bars are 100 µm). Quantitative image analysis revealed that presence of 0, 18, 25, 62, 210 to 393 individual cells per image, respectively.

Figure 14:
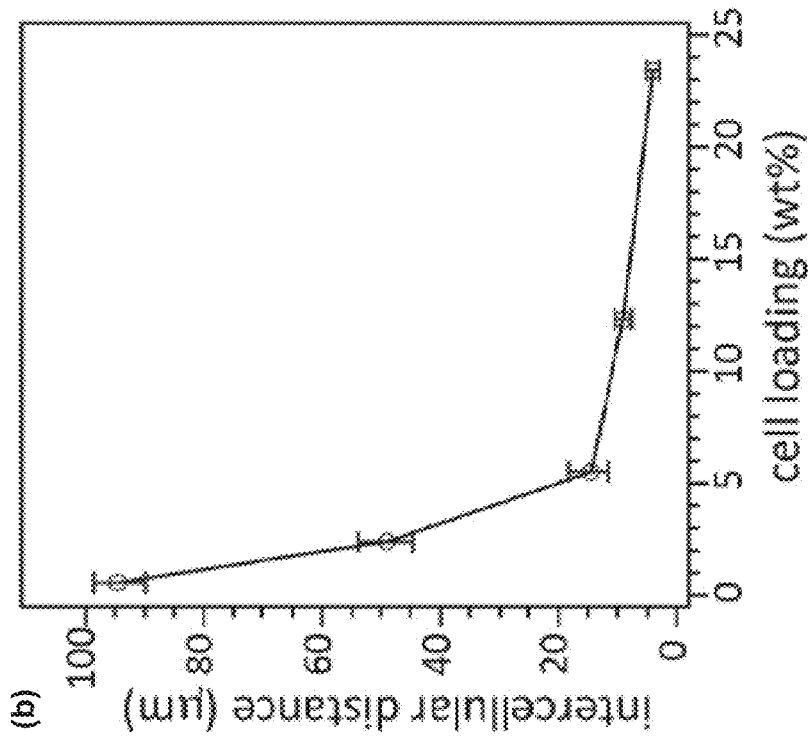
FIGS. 14A and 14B are representative graphs of calculated cell densities and intercellular distances of printed structures.
Figure 14:
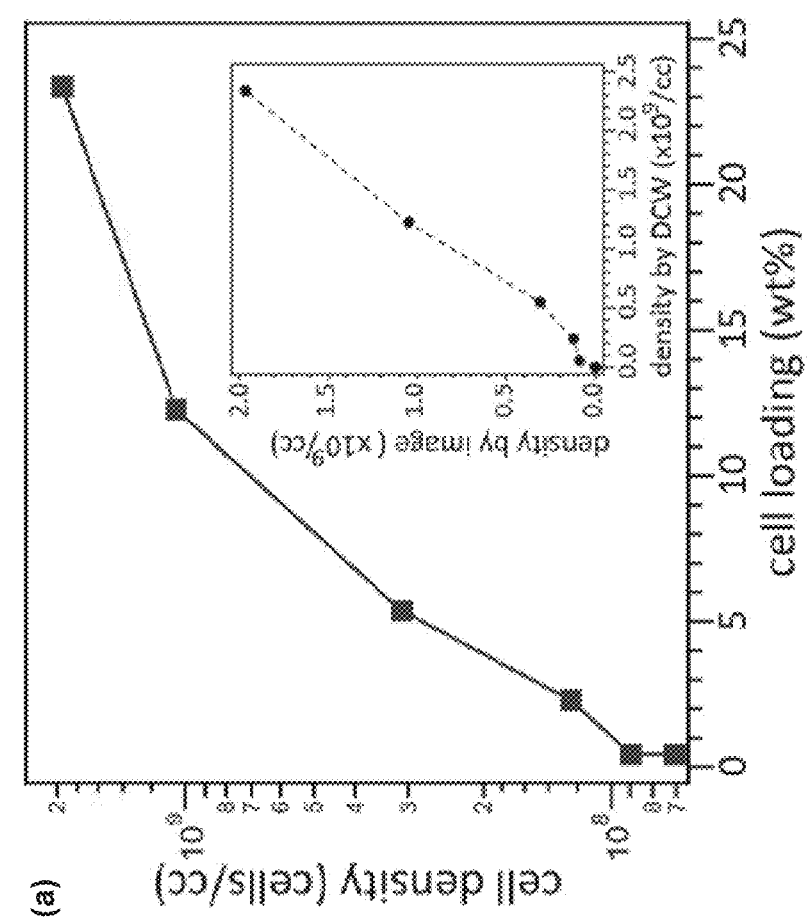

Based on the volume of the confocal slide, cell densities were derived from the image analysis. FIG. 14A shows calculated cell densities from the image analysis as a function of cell loading. Increasing cell loading in the bio-ink yielded a linear increase in cell density as expected. In addition, this curve can be used to calculate the dry cell weight (DCW) needed to prepare a bio-ink for a desired cell density. Correlation of cell densities calculated from image analysis and those from DCW shows a linear correlation (FIG. 14G, inset) with a slightly lower cell density calculated from image analysis as compared to that estimated from DCW. This discrepancy is attributed to the expansion, in volume, of PEGDA-based after they have been fully hydrated. Lastly, together with the increase of cell loading/cell densities in the bio-ink, FIG. 14B shows that intercellular distance drastically decreases accordingly. In the printed structure with a 23.4 wt % cell loading, the calculated cell density from the image was $1.9 \times 10^9$ cells/cm$^3$, while the mean cell-to-cell distance was reduced to 4.3 µm, approaching the single-cell length scale.

Example 6: Catalytic Studies

Printed yeast lattices were tested for their ability to convert glucose into ethanol and $CO_2$, the primary fermentation pathway in *S. cerevisiae*, according to the following equation:

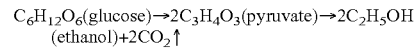

$$C_6H_{12}O_6 (\text{glucose}) \rightarrow 2C_3H_4O_3 (\text{pyruvate}) \rightarrow 2C_2H_5OH (\text{ethanol}) + 2CO_2\uparrow$$

Importantly, unlike previous work, the preparation of the bio-inks using freeze-dried cells provided structures with extremely high cell loadings of up to 42.8 wt % (or 75 vol %), where a high cell loading can provide enhanced productivity and catalytic performance. To determine the catalytic activity of the printed scaffolds and the solid bio-inks towards glucose fermentation, a quantitative ethanol essay was used. The printed structures were immersed in separate vials containing 3 mL YPD medium and cultured at 35° C. A 100 µL aliquot was taken from each vial every 10-15 minutes, and ethanol concentrations were measured via gas chromatography/mass spectrometry (GC/MS) using an Agilent Pora-PLOT Q column. Ethanol standards were used to derive calibration curves.

In the presence of glucose, printed scaffolds immediately produce ethanol and carbon dioxide gas ($CO_2$), as evidenced by rapid gas bubble generation from the scaffolds as well as quantitative ethanol assay. The printed porous scaffolds exhibited enhanced activity in the printed lattices in comparison to bulk hydrogel counterparts. This indicates that the mass transfer limit at high cell densities can be overcome by printing optimized structures with rationally designed pore geometries.

Figure 15:
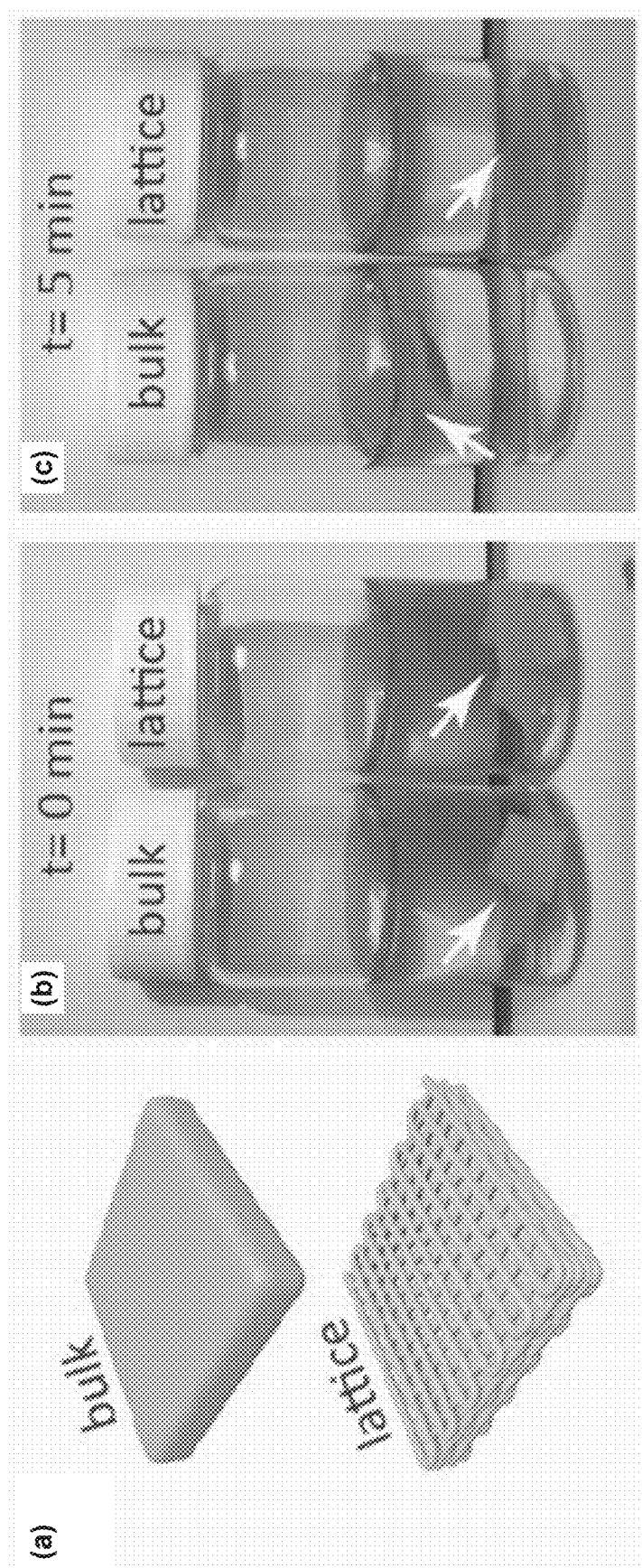
FIG. 15A is a representative schematic of bulk and printed structures according to an embodiment of the present disclosure.
FIGS. 15B and 15C are representative photographs of bulk and printed structures immersed in growth media.

To determine how geometry impacts the catalytic activity of cells and productivity in a bioreactor, both porous lattices and bulk hydrogels (i.e., not porous) comprised of the same bio-ink material were prepared. Several identical porous lattices were printed having an area of 1 $cm^2$, a thickness of approximately 1.5 mm, and 200-µm resolution. In addition, bulk samples were made using the same bio-ink as the porous lattices by photo-curing a film with the same area and thickness. Each sample was pre-weighed prior to immersion into the medium in order to normalize for their catalytic performance (i.e., per 0.1 g of bio-ink used). FIG. 15A is a schematic of the bulk and printed lattices, highlighting the differences in the geometries of the two structures. The structures were then immersed in growth media at different time points. FIGS. 15B and 15C are photographs of the structures immediately after immersion (i.e., t=0) and after five minutes (i.e., t=5), respectively. In both the porous lattices and bulk structures, within a minute after submersion in fresh YPD medium, $CO_2$ gas bubbles were generated and released from the surface of hydrogels. However, $CO_2$ was released much faster from the lattices than from the bulk film controls. Further, the bulk films floated to the top of the liquid surface after several minutes of incubation, while the lattices remained submerged. This is attributed the efficient mass transfer exhibited by printed lattices as a result of the structural porosity and thin filaments. The structural porosity and thin filaments both lead to enhanced interfacial area at the liquid/hydrogel interface, where the exchange of the nutrients, products and/or gas is rapid. At the cell level, once $CO_2$ is generated from the cells, it rapidly diffuses through the fine filament and is released into the medium. In contrast, for bulk films, the average diffusion length of $CO_2$ inside the material is substantially larger than the thin filament of lattices and thus, the gas diffusion is slow. Due to this slow gas diffusion, the gas bubbles are trapped inside the structure and cause the bulk structures to float to the top of the liquid surface.

Figure 16:
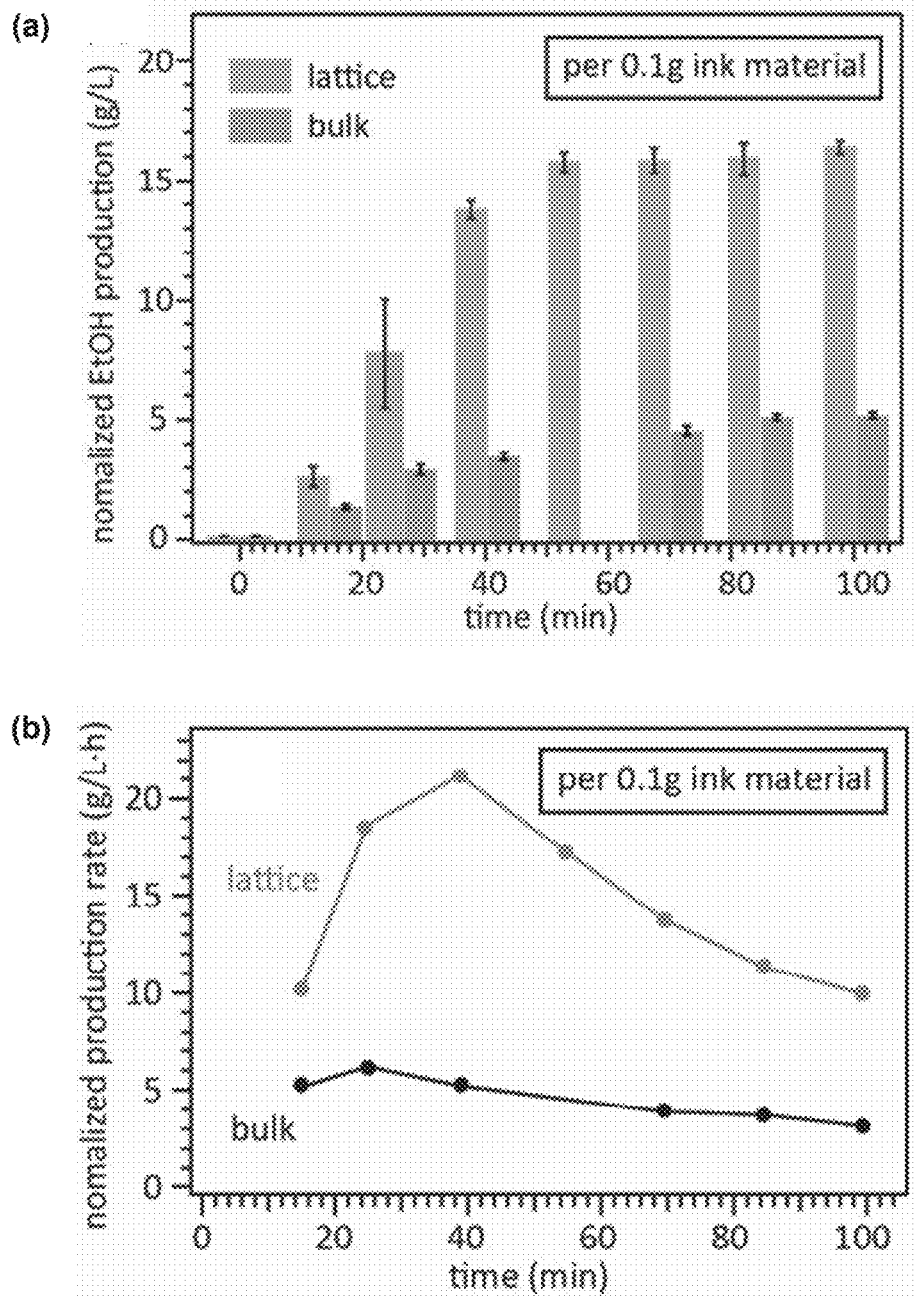
FIGS. 16A and 16B are representative graphs depicting the volumetric productivity of ethanol of the bulk and printed structures.

Quantitative measurements of ethanol production were consistent with this observation. To measure the concentration of ethanol, each sample was immersed in an individual vial containing YPD medium. Ethanol production from printed lattices and bulk films, normalized by the weight of the bio-ink used, are shown in FIG. 16A. After a short lag period, both the porous lattice and bulk structures produced ethanol. However, the porous lattices rapidly produced ethanol with the reaction reaching completion in less than an hour due to glucose depletion coincident with a decrease in $CO_2$ generation. At the end of the reaction, the lattices, on average, generated 16.1 g/L ethanol per 0.1 g ink material, and the final concentration in the spent medium was about 3.7 v/v %. In contrast, the bulk structures produced 5.1 g/L ethanol per 0.1 g ink material, less than one-third of the lattice production as shown in FIG. 16A. This is attributed to the poor mass transfer in bulk hydrogels, limiting glucose access and causing metabolic waste accumulation, which both negatively impact the culture microenvironment. Furthermore, FIG. 16B shows that ethanol productivity in the lattices reached a maximum rate of 21 g ethanol/L·h in 40 min and then started to decrease as glucose was depleted whereas the bulk structures exhibited a consistent production of 5 g ethanol/L·h throughout the duration of the experiment.

The ethanol yield observed in the bio-ink structures is higher as compared to previously prepared cell-laden scaffolds used for glucose bioconversion to ethanol (i.e., 1.5 v/v % of ethanol for 2 wt % glucose). This is potentially due to increased cell density and mass transfer, although other factors including strain, medium, and growth condition differences may also contribute to the observed catalytic enhancement. These results demonstrate that in hydrogels loaded with high cell densities (i.e., bulk structures), mass transport limits the catalytic reaction.

Figure 17:
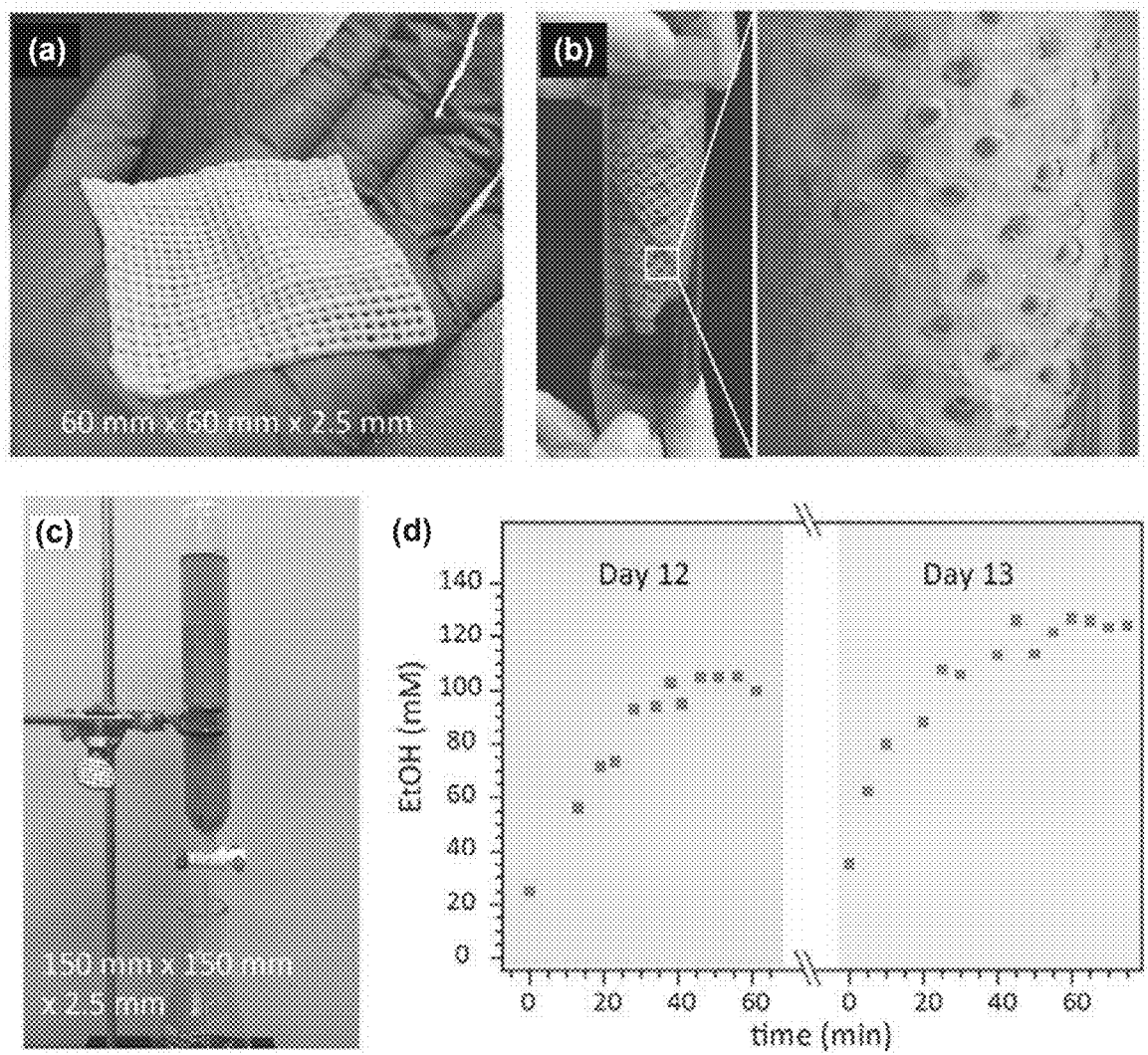
FIG. 17A is a representative photograph of a large-scale printed structure.
FIG. 17B is a representative photograph of the printed structure shown in FIG. 17A rolled into a tube.
FIG. 17C is a representative photograph of a large-scale printed structure rolled into a column.
FIG. 17D is a representative graph depicting the ethanol production of the printed structure in FIG. 17C.

To demonstrate the potential of 3D printed microbial structures to be integrated with existing large-scale industrial infrastructure, the structures were printed with increased dimensions and subsequently studied for their long-term effect on cell culture and cell/material interactions. Practical applications such as producing large quantities of products using catalytic microorganisms were performed in pilot-scale bio-tanks in a batch-fed mode or continuous-flow mode. FIG. 17A shows a palm-sized mat scaffold printed through a 0.6 mm nozzle, with an area of 36 $cm^2$ and a total thickness of 0.25 cm. The mat was then rolled up to fit into a 50-ml falcon tube and immersed in YPD medium with the cap closed as shown in FIG. 17B. A significant amount of $CO_2$ bubbles was rapidly generated from the scaffold where the rapid gas generation in a closed system pressurized the vessel, which, upon opening the cap, resulted in gas release and a release of dissolved $CO_2$.

Based on these results, the printing scale was further increased to produce a 15 cm×15 cm×0.25 cm mat scaffold, which was rolled up and inserted into a chromatography column, a configuration that could be leveraged for both batch and continuous-flow operations as shown in FIG. 17C. This scaffold was incubated at room temperature and fed every other day. $CO_2$ bubbles were produced upon medium exchange and were used as a qualitative measure of cell activity. As depicted in FIG. 17D, total ethanol production was measured on day 12 (left) and day 13 (right) and showed a consistent titer and dynamic profile during this timeframe. Upon medium replenishment, the ethanol concentration increased within an hour, consistent with the visual observation of $CO_2$ generation. The final ethanol concentration in the medium was detected as about 120 mM, corresponding to a 0.7 v/v % of ethanol. The ethanol yield is lower than the value achieved in small-scale lattices (3.7 v/v %), potentially due to large filament size, unoptimized culture conditions, cell aging, substrate limitation, etc. Synergistic optimization of scaffold geometry, bioreactor design, and culture conditions are needed to improve the reactor performance when scaled.

Figure 18:
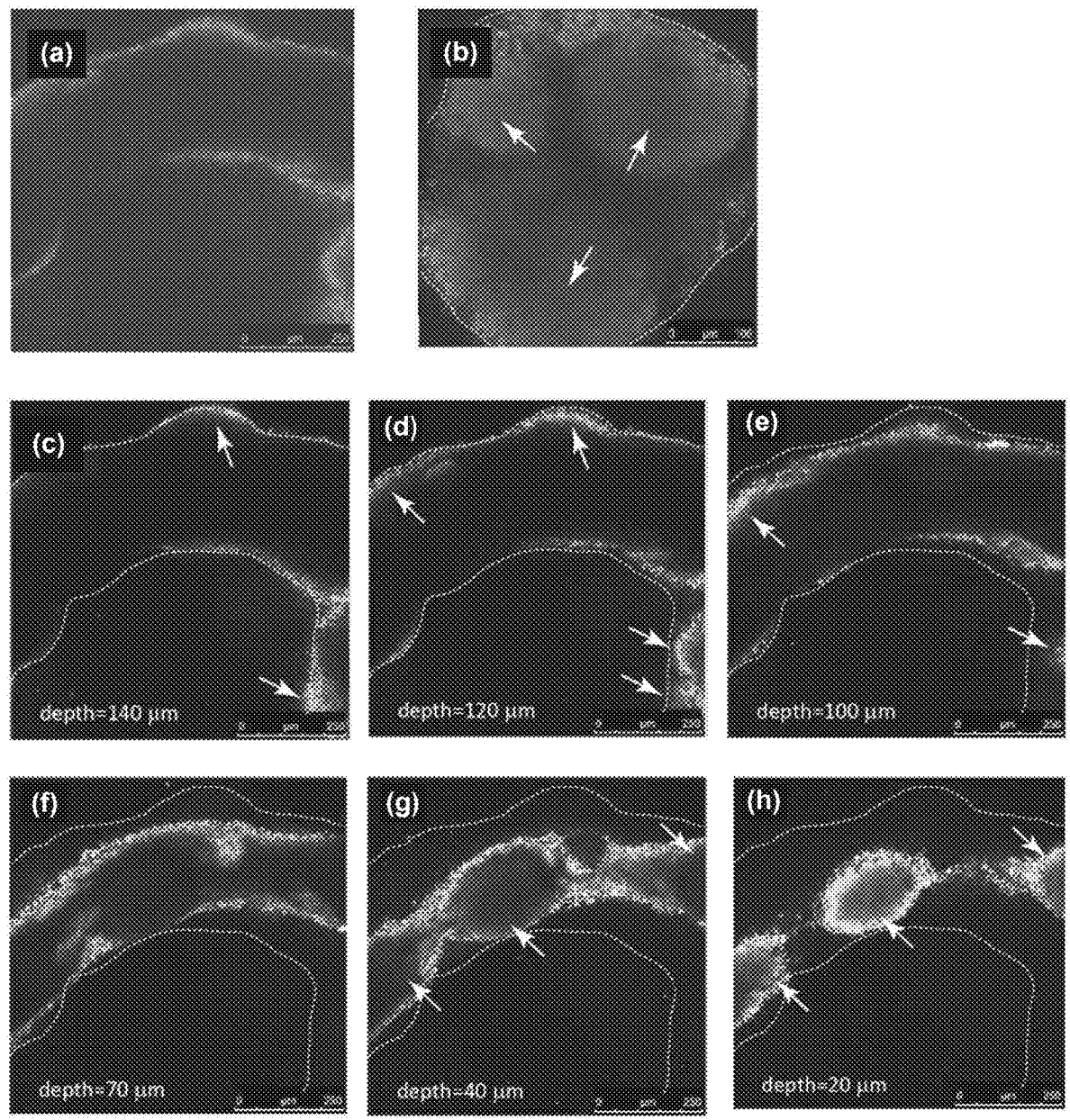
FIGS. 18A-18H are representative confocal images of a printed structure cultured for a month.
Figure 19A:
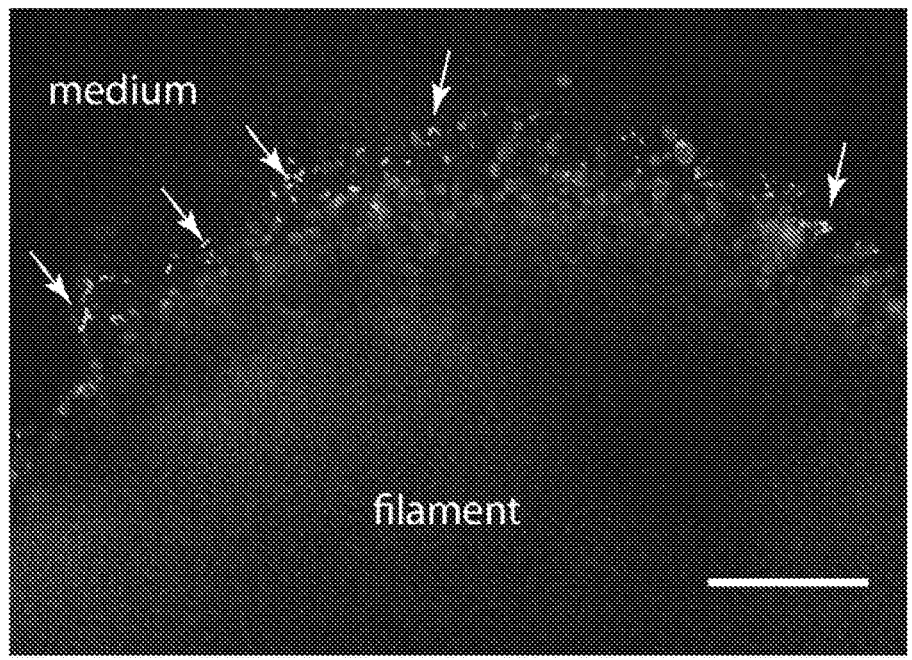
FIGS. 19A-19B are representative confocal images taken from two different sites of the printed structure in FIGS. 18A-18H.
Figure 19B:
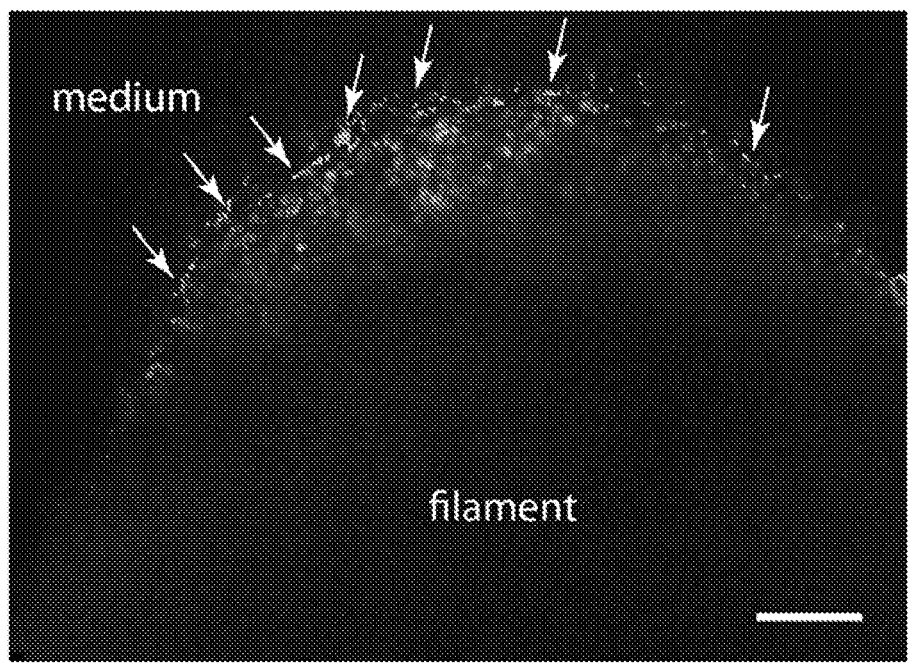

The cell viability and spatial distribution were examined in a scaffold that had been cultured for a month with observable glucose fermentation activity. A series of confocal images taken at different depths of a section of 200-μm filament are shown in FIGS. 18A-18H (scale bars are 250 μm). Compared to freshly printed scaffolds featuring smooth filament surface and uniform cell distribution as depicted in FIGS. 11A-11F, 12A-12C, and 13A-13F, the scaffold filament surface became bumpy after a month of incubation as shown in FIG. 18A, indicating a change in the biomaterial homogeneity (scale bars are 250 μm). In FIG. 18B, shows the cross-sectional image of a printed filament, in which three observable live colonies (scale bars are 100 μm) where the dotted white lines indicate a hydrogel/liquid interface and the white arrows highlight the position of three live cell colonies. Confocal microscope images shown in FIGS. 18C-18H with live-dead staining showed that the bumps consisted of live cell colonies, with an average size of 100-200 μm, still encapsulated in the hydrogel both inside and at the surface of filaments (scale bars are 250 μm). In FIGS. 18C-18H, the dotted white lines indicate the edge of the filament and the white arrows highlight the position of live cell colonies. In addition to *S. cerevisiae* cells with a characteristic 4-μm spherical shape, FIG. 19 shows the presence of bacterial cells (rod-shaped, approximately 1 μm in length). These bacterial cells do not penetrate, and appear on the filament surface, suggesting that bacterial contamination occurred post-printing, that they did not cross the hydrogel/liquid interface, and that the printed structures may provide some degree of physical protection of encapsulated cells from contaminants. Cultured under a non-optimized, non-sterile condition for 4 months, the printed scaffold shown in FIG. 17 still generated $CO_2$ immediately after the addition of fresh medium, despite an apparent decrease in activity. These observations provide new insights into the long-term culture of printed living materials as biocatalysts.

The cell-laden scaffolds were observed to be metabolically active for 4 months; during this period, encapsulated cells re-distributed themselves via local proliferation. These results demonstrate that printing of live, whole-cells can serve as a versatile platform for fundamental studies of microbial behaviors, communications and interaction with the environment, and also suggest substantial potential in highly-efficient, customized 3D bioreactors with enhanced volumetric productivity, long life-time, and simplified product separation.

Together these data illustrate the development of a new bio-ink comprised of freeze-dried live cells that enables the additive manufacturing of a self-supported 3D structure with a high resolution, high cell density, and large surface area/and or volume. The bio-ink having volumetric cell loading exhibits shear-thinning behavior, a desired property for extrusion-based cell printing. The addition a second filler (e.g., nanocellulose) to the bio-ink provides a method to rationally tune the cell density of the bio-ink while maintaining the desired properties for printing. The 3D structures are able to catalyze the fermentation of glucose with a 3× and 4× increase in ethanol production as compared to previous structures. The increase in catalytic activity is attributed to the ability to print the structures with thin filaments and produce macro-pores which allow for rapid mass transfer at the solid-liquid interaction.

Para A. A bio-ink comprising a filler of freeze-dried cells.

Para B. The bio-ink of Para. A, wherein the filler of freeze-dried cells are microbes.

Para C. The bio-ink of Para. A or Para. B., wherein the microbes are selected from the group consisting of bacteria, algal, fungi, protozoa, and a mixture thereof.

Para D. The bio-ink of any one of Paras. A-C, wherein the filler of freeze-dried cells has a cell density of at least about 5 wt %, about 10 wt %, about 20 wt %, about 30 wt %, about 40 wt %, about 50 wt %, about 60 wt %, about 70 wt %, about 75 wt %, about 80 wt % about 90 wt %, about 95 vol %, or more of the total weight of the bio-ink.

Para E. The bio-ink of any one of Paras. A-D, wherein the filler of freeze-dried cells has a cell density of at least about 5 vol %, about 10 vol %, about 20 vol %, about 30 vol %, about 40 vol %, about 50 vol %, about 60 vol %, about 70 vol %, about 75 vol %, about 80 vol %, about 85 vol %, about 90 vol %, about 95 vol %, or more of the total volume of the bio-ink.

Para F. The bio-ink of any one of Paras. A-E, wherein the filler is a single filler.

Para G. The bio-ink of any one of Paras. A-F, wherein the filler is a dual filler.

Para H. The bio-ink of any one of Paras. A-G, wherein the dual filler comprises freeze-dried live cells and a dual filler component.

Para I. The bio-ink of any one of Paras. A-H, wherein the dual filler component is selected from the group consisting of cellulose, a plastic, a ceramic, and a metal.

Para J. The bio-ink of any one of Paras. A-I, wherein the cellulose is selected from the group consisting of nanocellulose, cellulose nanocrystals (CNC), cellulose nanofibrils (CNF), bacterial cellulose (BC), and nanocellulose crystalline powder.

Para K. The bio-ink of any one of Paras. A-J, further comprising a hydrogel.

Para L. The bio-ink of Para. K, wherein the hydrogel is selected from the group consisting of polyethylene glycol dimethacrylate (PEGDA), polyethylene glycol, alginate, gelatin, glycidyl methacrylate, pluronic F127-di-acrylate (F127-DA), pluronic F127-di-methyl acrylate (F127-DMA), and gelatin methacryloyl.

Para M. The bio-ink of any one of Paras. A-L, wherein the filler further comprises a binder and/or a photo-initiator.

Para N. The bio-ink of any one of Paras. A-M, wherein the bio-ink is thixotropic.

Para O. The bio-ink of any one of Paras. A-N, wherein the bio-ink is viscoelastic.

Para P. A method of making a living structure comprising use of the bio-ink of any one of Paras. A-O.

Para Q. The method of Para. P, further comprising seeding at least one additional cell into the living structure.

Para R. A living structure made from a bio-ink comprised of a filler of freeze-dried cells.

Para S. The living structure of Para. R, wherein the living structure is biocompatible.

Para T. The living structure of Para. R or Para. S, wherein the living structure is three dimensional (3D), a lattice, a scaffold, and/or porous.

Para U. The living structure of any one of Paras. R-T, wherein at least a portion of the freeze-dried cells are encapsulated in the living structure.

Para V. The living structure of any one of Paras. R-U, wherein the living structure maintains cell viability and/or is metabolically active for at least about 1 month, about 2 months, about 3 months, 4 months, about 6 months, about 8 months, or about 10 months.

Para W. The living structure of any one of Paras. R-V, wherein the living structure of freeze-dried cells has a cell density of at least about 5 wt %, about 10 wt %, about 20 wt %, about 30 wt %, about 40 wt %, about 50 wt %, about 60 wt %, about 70 wt %, about 75 wt %, about 80 wt %, about 90 wt %, about 95 wt %, or more of the total weight of the bio-ink.

Para X. The living structure of any one of Paras. R-W, wherein the living structure has a cell density of at least about 5 vol %, about 10 vol %, about 20 vol %, about 30 vol %, about 40 vol %, about 50 vol %, about 60 vol %, about 70 vol %, about 75 vol %, about 80 vol %, about 85 vol %, about 90 vol %, about 95 vol %, or more of the total volume of the bio-ink.

Para Y. The living structure of any one of Paras. R-X, wherein the filler of freeze-dried live cells are microbes.

Para Z. The living structure of any one of Paras. R-Y, wherein the microbes are selected from the group consisting of bacteria, algal, fungi, and prokaryotes.

Para AA. The living structure of any one of Paras. R-Z, wherein the filler is a single filler.

Para BB. The living structure of any one of Paras. R-AA, wherein the filler is a dual filler.

Para CC. The living structure of any one of Paras. R-BB, wherein the living structure has a cube, cylinder, hollow cone, or circular translating coil geometry.

Para DD. The living structure of any one of Paras. R-CC, wherein the living structure has a resolution of at least about 10 μm, 20 μm, about 40 μm, about 50 μm, about 80 μm, about 100 μm, about 200 μm, about 300 μm, about 400 μm, and about 500 μm.

Para EE. The living structure of any one of Paras. R-DD, wherein living structure has a tunable cell density.

Para FF. The living structure of any one of Paras. R-EE, wherein the living structure has a volume between about 1 cm$^3$ to and about 600 cm$^3$.

Para GG. The living structure of any one of Paras. R-FF, wherein the living structure has an area of at least about 225 cm$^2$.

Para HH. The living structure of any one of Paras. R-GG, wherein the living structure facilities cell nutrient acquisition.

Para II. The living structure of any one of Paras. R-HH, wherein the living has a structure tunable intercellular distance.

Para JJ. The living structure of any one of Paras. R-II, wherein the living structure is catalytic.

Para KK. The living structure of any one of Paras. R-JJ, wherein the living structure exhibits high mass transport.

Para LL. A method of using a living structure made from a filler comprised freeze-dried cells for biosensing, tissue regeneration, environment sensing, drug discovery, catalysis, and/or clinical implementation.

Para MM. The method of Para. LL, wherein the living structure simulates an in vivo cell environment.

Para NN. The method of Para. LL or Para. MM, wherein the living structure mimics morphology, intercellular interactions, signaling pathway activation, and/or diffusion of cells.

Para OO. The method of any one of Paras. LL-NN, wherein the living structure performs cellular functions selected from the group consisting of cell proliferation, gene expression, protein expression, and responding to external stimuli.

Para PP. The method of any one of Paras. LL-OO, wherein the living structure can detect a change in a surrounding environment.

Para QQ. The method of Para. PP, wherein the change is fluctuations in at least one analyte.

Para RR. The method of Para. QQ, wherein the at least one analyte is selected from the group consisting of pathogens, proteins, DNA, and toxins.

Para SS. The method of any one of Paras. LL-RR, wherein the catalysis is biocatalysis.

Para TT. The method of Para. SS, wherein the biocatalysis includes food fermentation, biofuel production, protein synthesis, wastewater treatment, and/or bioremediation.

Para UU. The method of any one of Paras. LL-TT, wherein the living structure can carry out glucose fermentation.

Para VV. The method of any one of Paras. LL-UU, wherein the living structure is biocompatible.

Para WW. The method of any one of Paras. LL-VV, wherein the living structure is a tissue or organ.

We claim:

1. A bio-ink comprising:
   a first filler component comprising freeze-dried cells, wherein the first filler component of freeze-dried cells has a cell density of at least about 10 vol % or more of the total volume of the bio-ink, and
   a second filler component comprising nanocellulose crystalline powder,
   wherein the bio-ink is configured to be used for bioprinting three-dimensional structures including living cells.

2. The bio-ink of claim 1, wherein the first filler component of freeze-dried cells are microbes, wherein the microbes are selected from the group consisting of bacteria, algae, fungi, protozoa, and a mixture thereof.

3. The bio-ink of claim 1, wherein the first filler component of freeze-dried cells has a cell density of at least about 20 vol % or more of the total volume of the bio-ink.

4. The bio-ink of claim 1, wherein the first filler component of freeze-dried cells has a cell density of at least about 40 vol % or more of the total volume of the bio-ink.

5. The bio-ink of claim 1, wherein the first filler component of freeze-dried cells has a cell density of at least about 60 vol % or more of the total volume of the bio-ink.

6. The bio-ink of claim 1, wherein the first filler component of freeze-dried cells has a cell density of at least about 80 vol % or more of the total volume of the bio-ink.

7. A bio-ink comprising:
   a first filler component comprising freeze-dried cells, wherein the first filler component of freeze-dried cells has a cell density of at least about 10 wt % of the total weight of the bio-ink and
   a second filler comprising nanocellulose crystalline powder,
   wherein the bio-ink is configured to be used for bioprinting three-dimensional structures including living cells.

8. The bio-ink of claim 7, wherein the first filler component of freeze-dried cells are microbes, and wherein the microbes are selected from the group consisting of bacteria, algae, fungi, protozoa, and a mixture thereof.

9. The bio-ink of claim 7, wherein the first filler component of freeze-dried cells has a cell density of at least about 20 wt % or more of the total weight of the bio-ink.

10. The bio-ink of claim 7, wherein the first filler component of freeze-dried cells has a cell density of at least about 40 wt % or more of the total weight of the bio-ink.

11. The bio-ink of claim 7, wherein the first filler component of freeze-dried cells has a cell density of at least about 60 wt % or more of the total weight of the bio-ink.

12. The bio-ink of claim 7, wherein the first filler component of freeze-dried cells has a cell density of at least about 80 wt % or more of the total weight of the bio-ink.

13. A bio-ink comprising:
   a first filler component comprising freeze-dried cells, wherein the first filler component of freeze-dried cells has a cell density of at least about 10 vol % or more of the total volume of the bio-ink, a second filler component selected from the group consisting of nanocellulose, cellulose nanocrystals (CNC), cellulose nanofibrils (CNF), and nanocellulose crystalline powder,
wherein the bio-ink is configured to be used for bio-printing three-dimensional structures including living cells, and
a binder comprising an oligomer, monomer, or a combination thereof, wherein the binder is configured to form a polymer when the bio-ink is used for bio-printing the three-dimensional structures including living cells.

14. The bio-ink of claim 13, wherein the binder comprises styrene, methacrylate, vinyl alcohol, polyisobutylene, glycerol, polypropylene, or polyethylene glycol dimethacrylate.

15. The bio-ink of claim 13, further comprising a photo-initiator configured to initiate photopolymerization of the binder upon irradiation with light.

16. The bio-ink of claim 15, wherein the photo-initiator comprises 1-hydroxycyclohexyl phenyl ketone, 2,2-dimethoxy-2-phenylacetophenone, 2-methyl-1-[4-(-methylthio)phenyl]-2-4-morpholinyl)-1-propanone, hydroxyacetophenone, phosphineoxide, benzophenone, or lithium phenyl-2,4,6-trimethylbenzoylphosphinate (LAP).

17. The bio-ink of claim 13, wherein the first filler component of freeze-dried cells are microbes, wherein the microbes are selected from the group consisting of bacteria, algae, fungi, protozoa, and a mixture thereof.

18. The bio-ink of claim 13, wherein the first filler component of freeze-dried cells has a cell density of at least about 20 vol % or more of the total volume of the bio-ink.

19. The bio-ink of claim 13, wherein the first filler component of freeze-dried cells has a cell density of at least about 40 vol % or more of the total volume of the bio-ink.

20. The bio-ink of claim 13, wherein the first filler component of freeze-dried cells has a cell density of at least about 60 vol % or more of the total volume of the bio-ink.

* * * * *